United States Patent
Yoshitake et al.

(10) Patent No.: US 6,334,097 B1
(45) Date of Patent: Dec. 25, 2001

(54) METHOD OF DETERMINING LETHALITY OF DEFECTS IN CIRCUIT PATTERN INSPECTION METHOD OF SELECTING DEFECTS TO BE REVIEWED AND INSPECTION SYSTEM OF CIRCUIT PATTERNS INVOLVED WITH THE METHODS

(75) Inventors: Yasuhiro Yoshitake, Yokosuka; Masataka Shiba, Yokohama; Atsushi Shimoda, Hiratsuka, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/225,513

(22) Filed: Jan. 6, 1999

(30) Foreign Application Priority Data

Jan. 22, 1998 (JP) ................................. 10-010456

(51) Int. Cl.[7] .................................... G06F 11/32
(52) U.S. Cl. .......................... 702/185; 324/512
(58) Field of Search .................... 702/183, 185, 702/184, 83, 33, 34, 35, 36, 40, 81–84, 108, 117, 118, 119, 120, 121, 170, 172, 182; 324/500, 537, 750, 753, 71, 751; 325/512; 340/500, 635; 716/5; 706/47, 48

(56) References Cited

U.S. PATENT DOCUMENTS

| | | | |
|---|---|---|---|
| 5,680,207 | * 10/1997 | Hagiwara et al. | 356/237 |
| 5,744,381 | * 4/1998 | Tabata et al. | 438/16 |
| 5,991,699 | * 10/1999 | Kulkarni et al. | 702/83 |
| 5,995,219 | * 10/1999 | Tabata | 356/237.5 |
| 6,064,484 | * 5/2000 | Kobayashi et al. | 356/390 |

OTHER PUBLICATIONS

"An Advanced Yield Learning System for 64M DRAM Production and Beyond", Technical Proceedings SEMICON/Japan 1996, pp. (2–19)–(2–24).

* cited by examiner

*Primary Examiner*—Marc S. Hoff
*Assistant Examiner*—Edward Raymond

(57) ABSTRACT

From the coordinate data of defects detected on the circuit patterns, the areas where the defects belong are identified. The sizes of the defects detected are compared with the data to determine the lethality to thereby determine the lethality of the defects. Further, the severity of the defects is calculated from the sizes of the defects to thereby select the review object in the descending order of the severity.

Thereby, when inspecting the circuit patterns on a semiconductor wafer or the like, the lethality of the defects can automatically be determined even though the review is not carried out, enhancing the efficiency of the inspection. To perform the review with efficiency, the defects to be reviewed are automatically selected, while the quality of the inspection itself is maintained.

38 Claims, 17 Drawing Sheets

FIG. 3

| AREA NO | x1 | y1 | x2 | y2 | CLASS |
|---|---|---|---|---|---|
| 1 | 0 | 0 | 83 | 126 | 0 |
| 2 | 4 | 7 | 36 | 55 | 10 |
| 3 | 4 | 71 | 36 | 119 | 10 |
| 4 | 48 | 7 | 80 | 55 | 10 |
| 5 | 48 | 71 | 80 | 119 | 10 |
| 6 | 36 | 7 | 48 | 119 | 20 |
| 7 | 4 | 55 | 80 | 71 | 30 |
| 8 | 4 | 7 | 18 | 22 | 40 |
| 9 | 8 | 26 | 18 | 36 | 40 |
| 10 | 8 | 40 | 18 | 50 | 40 |
| 11 | 22 | 12 | 32 | 22 | 40 |
| 12 | 22 | 26 | 32 | 36 | 40 |
| 13 | 22 | 40 | 32 | 50 | 40 |

| CLASS VALUE L | LENGTH $R_L$ ($\mu m$) | AREA $R_S$ ($\mu m^2$) | BRIGHTNESS $R_B$ |
|---|---|---|---|
| 0 | 2 | 4 | L |
| 10 | 1 | 1 | L |
| 20 | 1.5 | 2.25 | M |
| 30 | 1.5 | 2.25 | M |
| 40 | 0.5 | 0.25 | S |

211 − 212 = 213

COORDINATE DATA OF DEFECTS IN THE CURRENT PROCESS

COORDINATE DATA OF DEFECTS IN THE PREVIOUS PROCESS

COORDINATE DATA OF DEFECTS REMAINING AFTER THE COORDINATE DATA OF DEFECTS IN THE PREVIOUS PROCESS ARE REMOVED FROM THOSE IN THE CURRENT PROCESS

CORRELATION BETWEEN TOTAL DEFECT NUMBER AND YIELD

CONTROL CHART BASED ON TOTAL DEFECT NUMBER

CORRELATION BETWEEN LETHAL DEFECT NUMBER AND YIELD

CONTROL CHART BASED ON LETHAL DEFECT NUMBER

METHOD OF DETERMINING LETHALITY OF DEFECTS IN CIRCUIT PATTERN INSPECTION METHOD OF SELECTING DEFECTS TO BE REVIEWED AND INSPECTION SYSTEM OF CIRCUIT PATTERNS INVOLVED WITH THE METHODS

BACKGROUND OF THE INVENTION

1. Field of the Invention

The present invention relates to a method of determining the lethality of defects in the circuit pattern inspection, a method of selecting defects to be treated as review objects, and the circuit pattern inspection system involved with these methods. Particularly, the invention relates to a method of efficiently determining, in a manufacturing process to form semiconductor devices on a semiconductor wafer, whether a defect detected by an appearance/particle inspection instrument is lethal in accordance with the characteristics of circuit patterns of the semiconductor devices, a method of efficiently selecting a defect that should be treated as a review object when defects are detected, in accordance with the characteristics of defects generated on each process, and the system involved with the above methods.

2. Description of the Related Art

In the semiconductor manufacturing process, it is essential for maintaining or enhancing the yield to detect the cause of a failure as quickly as possible and feedback the countermeasure to the process and/or the manufacturing facilities. In order to establish the countermeasure, it is important to detect a failure by an inspection instrument and analyze the inspection data.

As the conventional technique in this field, defects such as pattern shorts and a pattern missing which are generated on the wafer process, and particles are automatically inspected by, for example, the inspection instruments using an image processing and dark field irradiation by laser beams.

These inspection instruments output the coordinate data of defects and particles in the semiconductor wafer, and the sizes of the defects to an analysis system that stores these data. Next, the inspected wafer is moved onto a stage of an optical microscope or scanning electron microscope, the stage is moved to the position corresponding to the coordinate data of a detected defect, and the defect is classified by the magnified image thereof. This classification work is called the review.

This review has two objects.

One is to classify defects detected in accordance with the characteristics of the defects themselves, such as pattern missing, pattern shorts, film residue, particles, etc.

Another one is to determine whether a defect leads to a lethal defect for the function of the semiconductor device, and from the result to classify the defect into a lethal defect or non-lethal defect.

After completing the review, a review station outputs the classification identifiers predetermined in accordance with the classification and lethality/non-lethality of the defects themselves to the analysis system that analyzes the data.

The foregoing conventional technique has become an essential technique for enhancing the yield when forming circuit patterns on a semiconductor wafer through the micro fabrication.

On the process of manufacturing a semiconductor wafer, if a defect is detected, occasionally the defect cannot be any obstacle to the operation. If there are particles on the wafer, to regard all the semiconductor chips made therefrom as failure is to treat even the normally operating chips as failure. That is impractical.

Therefore, the determination as to whether the defect is lethal or not is specially important in the inspection process. However, the conventional technique involves the following problems in the determination of the defect being lethal or not.

In the conventional technique, the review and the determination of lethality are carried out by human hands and brains, and therefore, the work needs a considerable time, which will become a hindrance to enhancing the throughput of the total inspection process.

In regard to the determination of lethality, the inspector needs to have the knowledge of functions and structures of the circuit patterns of a defective area as well as the discrimination of the defects themselves, and the work is entrusted to specialists having those specific knowledge. Further, the determination criterion of lethality differs among these specialists, and the result of determination varies depending on the inspector, which is a problem.

If the determination of lethality by the review is not conducted at all on the pretext of the throughput, or the determination of only a part of defects is conducted, the following inconveniences will arise.

This problem will be described with reference to FIG. 19. FIG. 19 illustrates a graph in which a relation between the total number of defects and the yield is plotted, and a graph in which the total number of defects produced in time series on each of inspection wafers is plotted.

As shown in FIG. 19($a$), there is not a correlation between the total number of defects and the yield of the semiconductor chips, and thereby a significant control limit cannot be introduced. Here, the control limit signifies the number of defects that is provided for controlling the quality. The yield indicates the rate of non-defectives against all the chips on a wafer.

Accordingly, as shown in FIG. 19($b$), although the total defect number by each inspection wafer is plotted in time series to thereby predict the abnormality of the yield and to thereby take a countermeasure in an earlier stage, since the total defect number does not function as a monitor value, the setting of a control limit will not bring about a good detection of abnormality. In the example of this drawing, since the total defect number exceeds the control limit in every point, all the defects are to be determined as abnormal.

During the review, it is necessary to view an enlarged image by the optical microscope or scanning electron microscope, which accompanies the works of moving the stage, bringing the defect into the field of view, focusing and the like. Therefore, to carry out the reviews of all the defects detected by the inspection instrument will be a contradiction against the requirement for enhancing the throughput in the inspection process. Accordingly, it is necessary to reduce the number of the defects of the review object, however, this work to reduce the number is entrusted to the review operator; and the selection results of the review object will differ depending on the operators, which is a problem.

The present invention has been made to resolve the foregoing problems, and it is therefore an object of the invention to provide a method of determining the lethality of defects, which enhances the efficiency of inspection by automatically determining the lethality of defects without conducting the review when inspecting circuit patterns formed on a substrate of a semiconductor wafer or the like, and an inspection system to implement the same.

Another object of the invention is to provide a method of automatically selecting defects to be reviewed in order to efficiently perform the review in the inspection of the circuit patterns while maintaining the quality of the inspection itself, and an inspection system to implement the same.

SUMMARY OF THE INVENTION

In order to accomplish the foregoing objects, the invention sets forth a construction relating to a method of determining a lethality of defects in an inspection of circuit patterns formed on a substrate, as follows. At an inspection stage, inspection data of the defects produced on the circuit patterns are generated, the inspection data generated are inputted to be processed; and thereby, the lethality of the defects corresponding to the inspection data are determined.

In detail, the foregoing method of determining the lethality employs the coordinate data of the circuit patterns and the sizes of the defects as the inspection data.

Further in detail, the foregoing method of determining the lethality of defects segments each of the circuit patterns into several areas having different characteristics, and serves the data to determine the lethality of the defects as determination rules each provided for each of the areas of the circuit patterns.

To achieve the foregoing objects, the invention sets forth a further detailed construction relating to the method of determining a lethality of defects, as follows. When each of the circuit patterns is segmented into several areas having different characteristics, area coordinate data of the circuit patterns and data to determine the lethality of the defects produced in the areas on the circuit patterns are held, and the coordinate data of the defects detected and the sizes of the defects can be obtained at an inspection stage, the method of determining of a lethality of defects comprises the following steps.

(1) accepting the area coordinate data of the circuit patterns,
(2) accepting the data to determine the lethality of the defects produced in the areas on the circuit patterns,
(3) accepting the coordinate data of the defects detected on the circuit patterns and the sizes of the defects,
(4) identifying the areas to which the defects belong, from the coordinate data of the defects detected on the circuit patterns, and
(5) comparing the sizes of the defects detected with the data to determine the lethality of the defects produced in the areas on the circuit patterns where the defects belong to thereby determine the lethality of the defects. After the step (1) through the step (3), the step (4) is executed, and thereafter the step (5) is executed.

In detail, the foregoing method of determining a lethality employs length data, area data, and brightness data which are served as indexes when detecting the defects as the sizes of the defects.

Further in detail, the foregoing method of determining a lethality employs pattern widths or pattern spaces in the areas as the data to determine the lethality of the defects produced in the areas on the circuit patterns.

Further in detail, in the foregoing method of determining a lethality, when the area coordinate data of the circuit patterns and pixel coordinates for display are brought into correspondence and inherent class values according to the characteristics of the areas are individually assigned to each of the areas, the foregoing step (4) is comprised of the steps of:
(4a) writing in advance class values in an array to express pixel coordinates,
(4b) obtaining the pixel coordinates corresponding to the coordinate data of the defects detected, and
(4c) determining the areas where the defects belong from the pixel coordinates.

To achieve the foregoing objects, the invention sets forth a construction relating to a method of selecting a review object of defects detected in an inspection of circuit patterns formed on a substrate, as follows. At an inspection stage, inspection data of the defects produced on the circuit patterns are generated, the inspection data generated are inputted to be processed; and thereby, the data to determine the lethality of the defects corresponding to the inspection data are generated, and the data to determine the lethality of the defects and the inspection data are compared, and thereby, the review object is selected among the defects produced.

In detail, the foregoing method of selecting a review object employs the coordinate data of the circuit patterns and the sizes of the defects as the inspection data.

Further in detail, the foregoing method of selecting a review object segments each of the circuit patterns into several areas having different characteristics, and serves the data to determine the lethality of the defects as determination rules each provided for each of the areas of the circuit patterns.

To achieve the foregoing objects, the invention sets forth a further detailed construction relating to the method of selecting a review object, as follows. When each of the circuit patterns is segmented into several areas having different characteristics, area coordinate data of the circuit patterns and data to determine the lethality of the defects produced in the areas on the circuit patterns are held, and coordinate data of the defects detected and sizes of the defects can be obtained at an inspection stage, the method of selecting a review object comprises the following steps.

(11) accepting the area coordinate data of the circuit patterns,
(12) accepting the data to determine the lethality of the defects produced in the areas on the circuit patterns,
(13) accepting the coordinate data of the defects detected on the circuit patterns and the sizes of the defects,
(14) identifying the areas to which the defects belong, from the coordinate data of the defects detected on the circuit patterns, and
(15) calculating ratios of the sizes of the defects detected against the data to determine the lethality of the defects produced in the areas on the circuit patterns where the defects belong. After the step (11) through the step (13), the step (14) is executed, thereafter the step (15) is executed, and the review object is selected, while the ratios are served as the indexes to indicate severity of the defects.

In detail, in the foregoing method of selecting a review object, the defects selected as the review object are confined to the defects corresponding to a specific number of the ratios obtained at the step (15), sorted in the descending order.

Further in detail, in the foregoing method of selecting a review object, the defects selected as the review object are the defects corresponding to the ratios which are obtained at the step (15) and have respectively a specific value or more.

Further in detail, the foregoing method of selecting a review object employs length data, area data, and brightness data which are served as indexes when detecting the defects as the sizes of the defects.

Further in detail, the foregoing method of selecting a review object employs pattern widths or pattern spaces in the areas as the data to determine the lethality of the defects produced in the areas on the circuit patterns.

Further in detail, in the foregoing method of selecting a review object, when the area coordinate data of the circuit patterns and pixel coordinates for display are brought into correspondence and inherent class values according to the characteristics of the areas are individually assigned to each of the areas, the foregoing step (14) is comprised of the steps of:

(14a) writing in advance class values in an array to express pixel coordinates, (14b) obtaining the pixel coordinates corresponding to the coordinate data of the defects detected, and (14c) determining the areas where the defects belong from the pixel coordinates.

Further in detail, the foregoing method of selecting a review object, in selecting the defects treated as the review object for each process, further comprises a step that compares coordinate data of the defects having been detected as the defects in a previous process to a process where the review is being executed at present with coordinate data of the defects having been detected as the defects in the concerned process where the review is being executed at present, and selects only the defects having non-coincident coordinate data in the result of the comparison as candidate defects of the review object in the concerned process where the review is being executed.

Further in detail, the foregoing method of selecting a review object further comprises a step that classifies the defects produced on the circuit patterns into cluster defects having a clustered mode and random defects produced at random from the mode in which the defects are produced, and selects the review object with different treatments for the cluster defects and the random defects.

Further in detail, the foregoing method of selecting a review object selects several defects of the cluster defects as the review object, and assumes the review result of the several defects as the review result of all the defects belonging to the cluster to thereby simplify the review for the cluster defects.

Further in detail, the foregoing method of selecting a review object, in selecting the defects treated as the review object for each process, when the cluster defects detected in the previous process and the cluster defects detected in the subsequent process have an overlapping part, treats both of the cluster defects as the cluster defects detected in the previous process.

In order to accomplish the foregoing objects, the invention sets forth a system of determining a lethality of defects in an inspection of circuit patterns formed on a substrate, which comprises: means to input inspection data of the defects produced on the circuit patterns, which are detected at an inspection stage; means to process the inspection data inputted; and means to determine the lethality of the defects corresponding to the inspection data.

In detail, the foregoing system of determining a lethality employs the coordinate data of the circuit patterns and the sizes of the defects as the inspection data.

Further in detail, the foregoing system of determining the lethality segments each of the circuit patterns into several areas having different characteristics, and serves the data to determine the lethality of the defects as determination rules each provided for each of the areas on the circuit patterns.

To achieve the foregoing objects, the invention sets forth a further detailed construction relating to the method of determining a lethality of defects, as follows. When each of the circuit patterns is segmented into several areas having different characteristics, the system comprises: an inspection instrument that obtains coordinate data of the defects detected and sizes of the defects, and an analysis system that analyzes the data to determine the lethality. The analysis system here includes a control unit, a memory to temporarily hold the data, a storage unit to permanently store the data, an operation unit, and an input/output interface. The analysis system further comprises: means to store the area coordinate data of the circuit patterns; means to store the data to determine the lethality of the defects produced in the areas on the circuit patterns; means to store the coordinate data of the defects detected on the circuit patterns and the sizes of the defects; means to identify the areas to which the defects belong, from the coordinate data of the defects detected on the circuit patterns; and means to compare the sizes of the defects detected with the data to determine the lethality of the defects produced in the areas on the circuit patterns where the defects belong to thereby determine the lethality of the defects.

In detail, the foregoing system of determining a lethality employs length data, area data, and brightness data which are served as indexes when detecting the defects as the sizes of the defects.

Further in detail, the foregoing system of determining a lethality employs pattern widths or pattern spaces in the areas as the data to determine the lethality of the defects produced in the areas on the circuit patterns.

Further in detail, in the foregoing system of determining a lethality, the inspection instrument and the analysis system are connected by a network, so that the data and commands can be exchanged.

Further in detail, in the foregoing system of determining a lethality, when the area coordinate data of the circuit patterns and pixel coordinates for display are brought into correspondence and inherent class values according to the characteristics of the areas are individually assigned to each of the areas, the analysis system, further containing a pixel coordinate storage unit, comprises means to write class values in an array to express the pixel coordinates, means to obtain the pixel coordinates corresponding to the coordinate data of the defects detected, and means to determine the areas where the defects belong from the pixel coordinates.

In order to accomplish the foregoing objects, the invention sets forth a system of selecting a review object of defects detected in an inspection of circuit patterns formed on a substrate, which comprises: means to input inspection data of the defects produced on the circuit patterns, which are detected at an inspection stage; means to process the inspection data inputted; means that generate the data to determine the lethality of the defects corresponding to the inspection data; and means that compare the data to determine the lethality of the defects with the inspection data. The system selects the review object among the defects produced, by using the means that compare the data to determine the lethality of the defects with the inspection data.

In detail, the foregoing system of selecting a review object employs the coordinate data of the circuit patterns and the sizes of the defects as the inspection data.

Further in detail, the foregoing system of selecting a review object segments each of the circuit patterns into several areas having different characteristics, and serves the data to determine the lethality of the defects as determination rules each provided for each of the areas of the circuit patterns.

In order to accomplish the foregoing objects, the invention sets forth a further detailed system of selecting a review object, which comprises: an inspection instrument that obtains coordinate data of the defects detected and sizes of the defects; and an analysis system that analyzes the data to select the review object. The analysis system includes a control unit, a memory to temporarily hold the data, a storage unit to permanently store the data, an operation unit, and an input/output interface, which further comprises: means to store the area coordinate data of the circuit patterns; means to store the data to determine the lethality of the defects produced in the areas on the circuit patterns; means to store the coordinate data of the defects detected on the circuit patterns and the sizes of the defects; means to identify the areas to which the defects belong, from the coordinate data of the defects detected on the circuit patterns; and means to calculate the ratios of the sizes of the defects detected against the data to determine the lethality of the defects produced in the areas on the circuit patterns where the defects belong. With this construction, the system of selecting a review object of the invention selects the review object, using the ratios as the indexes to indicate severity of the defects.

In detail, in the foregoing system of selecting a review object, the defects selected as the review object are confined to the defects corresponding to a specific number of the ratios obtained by the means to calculate the ratios, sorted in the descending order.

Further in detail, in the foregoing system of selecting a review object, the defects selected as the review object are the defects corresponding to the ratios obtained by the means to calculate the ratios and have respectively a specific value or more.

Further in detail, the foregoing system of selecting a review object employs length data, area data, and brightness data which are served as indexes when detecting the defects as the sizes of the defects.

Further in detail, the foregoing system of selecting a review object employs pattern widths or pattern spaces in the areas as the data to determine the lethality of the defects produced in the areas on the circuit patterns.

Further in detail, the foregoing system of selecting a review object further comprises a review station to perform the review; and the review station, the inspection instrument, and the analysis system are connected by a network, so that the data and commands can mutually be exchanged.

Further in detail, in the foregoing system of selecting a review object, the analysis system, further containing a pixel coordinate storage unit, comprises means to write class values in an array to express the pixel coordinates, means to obtain the pixel coordinates corresponding to the coordinate data of the defects detected, and means to determine the areas where the defects belong from the pixel coordinates.

Further in detail, the foregoing system of selecting a review object, in selecting the defects treated as the review object for each process, further comprises means that compare coordinate data of the defects having been detected as the defects in a previous process to a process where the review is being executed at present with coordinate data of the defects having been detected as the defects in the concerned process where the review is being executed at present, and selects only the defects having non-coincident coordinate data in the result of the comparison as candidate defects of the review object in the concerned process where the review is being executed.

Further in detail, the foregoing system of selecting a review object further comprises means that classify the defects produced on the circuit patterns into cluster defects having a clustered mode and random defects produced at random from the mode in which the defects are produced, and selects the review object with different treatments for the cluster defects and the random defects.

Further in detail, the foregoing system of selecting a review object selects several defects of the cluster defects as the review object, and assumes the review result of the several defects as the review result of all the defects belonging to the cluster to thereby simplify the review for the cluster defects.

Further in detail, the foregoing system of selecting a review object, in selecting the defects treated as the review object for each process, when the cluster defects detected in the previous process and the cluster defects detected in the subsequent process have an overlapping part, treats both of the cluster defects as the cluster defects detected in the previous process.

Based on the foregoing construction of the invention, the following effects will be achieved.

The foregoing method of determining a lethality makes it possible to automatically determine the lethality of the defects detected by the inspection instrument, without making a review of an enlarged image by using an optical microscope or scanning electron microscope. Accordingly, the determination of the lethality of the defects can be carried out at a high speed, and the lethality of all the defects detected can be determined.

Here, the advantage to determine the lethality of defects will be explained with reference to FIG. 20.

FIG. 20 illustrates a graph in which the relation between the number of defects determined as lethal and the yield is plotted, and a graph in which the number of defects determined as lethal that are produced in time series for each inspection wafer is plotted.

To determine the lethality of defects is to weight with a filter the defects determined as lethal from all the defects detected. If the lethality of the defects is determined and the number of the defects determined as lethal is obtained, as shown in FIG. 20(a), the number of the defects determined as lethal is found to possess a correlation with the yield of the chips. Therefore, a control limit can be introduced from the value of the yield, which is different from the case with the total defect number as shown in FIG. 19.

Accordingly, to control the abnormality of each inspection wafer with the number of the defects determined as lethal will detect abnormalities with a high accuracy. As shown in FIG. 20(b), when the number of lethal defects exceeds the control limit, the inspection wafer can be determined as abnormal. Thus, based on the control by the number of lethal defects, it becomes possible to detect abnormalities having correlation with the yield with a high accuracy, and thereby a countermeasure to raise the yield can be taken in an earlier stage.

In the foregoing description, the number of lethal defects is employed to control abnormalities, however, the rate of lethal defects may be employed. Here, the rate of lethal defects is the ratio of the number of the chips having lethal defects against the number of all the chips formed on the wafer.

Further, to correlate the area coordinates with the pixel coordinates, and assign in advance the class values to the pixel coordinate data makes it possible to swiftly determine the areas where the defects produced belong.

Next, according to the method of selecting a review object of defects detected in an inspection of circuit patterns of the invention, it becomes possible to automatically select a review object in the order of the importance of the review. Accordingly, the review can be performed with a high efficiency, while maintaining the quality of the review.

Further, the method of selecting a review object of the invention has a step that stores the coordinate data of the defects detected and the size data thereof, and thereafter, compares the coordinate data of the defects detected in the previous process with the coordinate data of the defects detected in the concerned process, and selects only the defects having non-coincident data as the defects produced in the concerned process.

Thereby, the defects already reviewed in the previous process cannot be selected again, thus avoiding a useless work.

Further, the method of selecting a review object of the invention has a step that classifies the defects having non-coincident coordinate data of the defects detected in the previous process and the defects detected in the concerned process into cluster defects and random defects from the coordinate data of the defects detected, and selects the defects to be reviewed from the defects thus classified.

Accordingly, the defects belonging to the same cluster that should be treated as the same classification cannot be selected repeatedly as the review object, thus eliminating a useless work.

Furthermore, the method of selecting a review object of the invention has a step that, after the classification of the cluster defects and random defects in the concerned process, compares the coordinate data of the cluster defects detected in the previous process with those of the cluster defects detected in the concerned process, and when the coordinate data of the cluster defects detected are coincident in more than one, puts all the defects contained in the clusters of the cluster defects in the previous process and the cluster defects in the concerned process into the same classification.

Thereby, the defects produced in the concerned process that result from the cluster defects produced in the previous process can be excluded from the review object, and a review result can be obtained with efficiency.

BRIEF DESCRIPTION OF DRAWINGS

FIG. 3 is a table to illustrate X-Y coordinates and class values corresponding to each of areas;

DETAILED DESCRIPTION OF PREFERRED EMBODIMENTS

The preferred embodiments relating to the invention will now be described with reference to FIG. 1 through FIG. 18.

The preferred embodiments will be described on the assumption of an example in which semiconductor devices are formed on a semiconductor wafer, and the similar technique can be applied to a process that manufactures a liquid crystal display, a thin film head for a hard disc drive, or the like.

First Embodiment

The first embodiment relating to the invention will be described with reference to FIG. 1 through FIG. 8.

First, referring to FIG. 1, the construction of the circuit pattern inspection system of this embodiment will be described.

Figure 1:
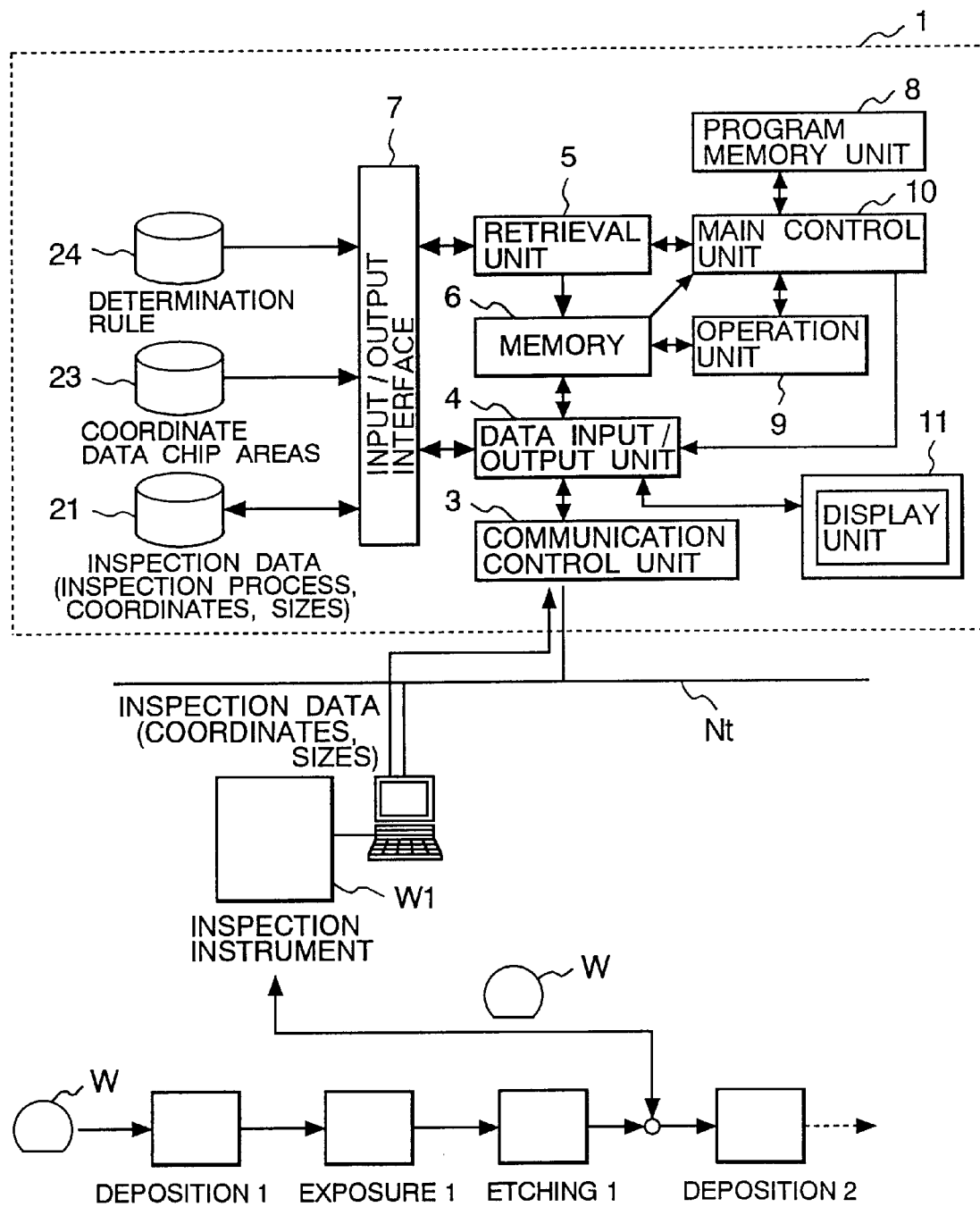
FIG. 1 is a block diagram of a circuit pattern inspection system relating to the first embodiment of the present a invention.

FIG. 1 is a chart to illustrate a system construction of the circuit pattern inspection system relating to the first embodiment of the invention.

The circuit pattern inspection system relating to this embodiment is comprised of an analysis system 1 and an inspection instrument WI, which are connected to each other through a network Nt that enables them to exchange the commands and the data.

The inspection instrument WI is equipment to inspect a semiconductor wafer W. The semiconductor wafer W is processed through a deposition system, exposure system, and etching system. Here, assuming that the semiconductor wafer W after etching is inspected, for example, the semiconductor wafer W is returned to the processing process that resumes from the deposition system. The data of the defects detected by the inspection instrument WI, for example, the coordinates of the defects, and the data of the sizes thereof are stored in an inspection data storage unit 21 provided in the analysis system 1.

On the other hand, the analysis system 1 is provided with a communication control unit 3, data input/output unit 4, retrieval unit 5, memory 6, input/output interface 7, program memory unit 8, operation unit 9, main control unit 10, display unit 11. Further, as the data storage, the analysis system 1 contains the inspection data storage unit 21, a storage unit for coordinate data chip areas 23, and a storage unit for determination rule data 24.

The communication control unit 3 is a part to control the communications by the foregoing network.

The data input/output unit 4 inputs/outputs data transmitted through the network.

The retrieval unit 5 has a function to retrieve the data stored in the inspection data storage unit 21, the storage unit for coordinate data chip areas 23, and the storage unit for determination rule data 24.

The memory 6 is a part to temporarily memorize the data retrieved by the retrieval unit 5.

The input/output interface 7 is an interface to coordinate the timing of data exchange with the inspection data storage unit 21, the storage unit for coordinate data chip areas 23, and the storage unit for determination rule data 24.

The main control unit 10 administers the whole controls in the analysis system 1, and the data input/output unit 4, retrieval unit 5, memory 6, operation unit 9, and program memory unit 8 are connected to the main control unit 10 and receive commands therefrom.

The program memory unit 8 contains programs as the software to execute necessary processing. The program is read out at any time by the main control unit 10 to be executed. On the basis of this program, the operation unit 9 executes necessary operations.

Figure 20A:
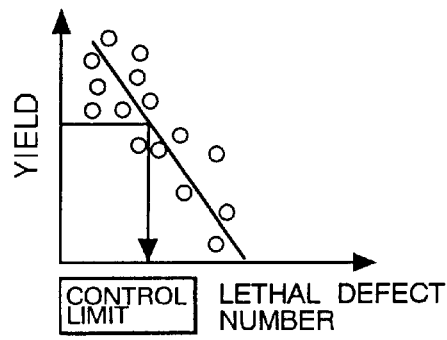
FIG. 20 illustrates a graph in which a relation between the number of defects determined as lethal and the yield is plotted, and a graph (control chart of the lethal defect number) in which the number of defects determined as lethal generated in time series on each of inspection wafers is plotted.
Figure 20B:
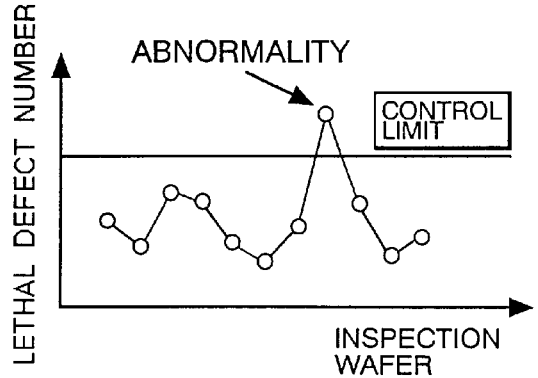

The display unit 11 is connected to the data input/output unit 4 to display the data from the inspection data storage unit 21, the storage unit for coordinate data chip areas 23, and the storage unit for determination rule data 24. The display unit 11 is able to display and confirm these various inspection data, and also able to display the control chart of the lethal defect number as shown in FIG. 20(b).

Further, the display unit 11 may be installed in a different place from the analysis system 1, and connected to the communication control unit 3 and data input/output unit 4 through the network Nt.

The inspection data storage unit 21, the storage unit for coordinate data chip areas 23, and the storage unit for determination rule data 24 normally store the data in the auxiliary storage units such as a hard disk, optical disk, and floppy disk; and these data may be stored in different storage media or in the same storage media.

Further, the analysis system 1 may be connected to a different system through the network Nt so as to transmit and receive the data of the inspection data storage unit 21, the storage unit for coordinate data chip areas 23, and the storage unit for determination rule data 24. The different system is, for example, a system to calculate a statistical data from these data.

Further, the analysis system 1 of this embodiment may be incorporated into the inspection instrument WI without the network Nt intervening between them.

The operation unit 9 and the main control unit 10 may be formed as one and the same semiconductor circuit, or as different semiconductor circuits. The retrieval unit 5, memory 6, data input/output unit 4, and communication control unit 3 may be formed as the same semiconductor circuit, or as different semiconductor circuits.

Next, the principle of the method of determining the lethality of defects in the circuit pattern inspection of this invention will be described with reference to FIG. 2 through FIG. 7.

Figure 2:
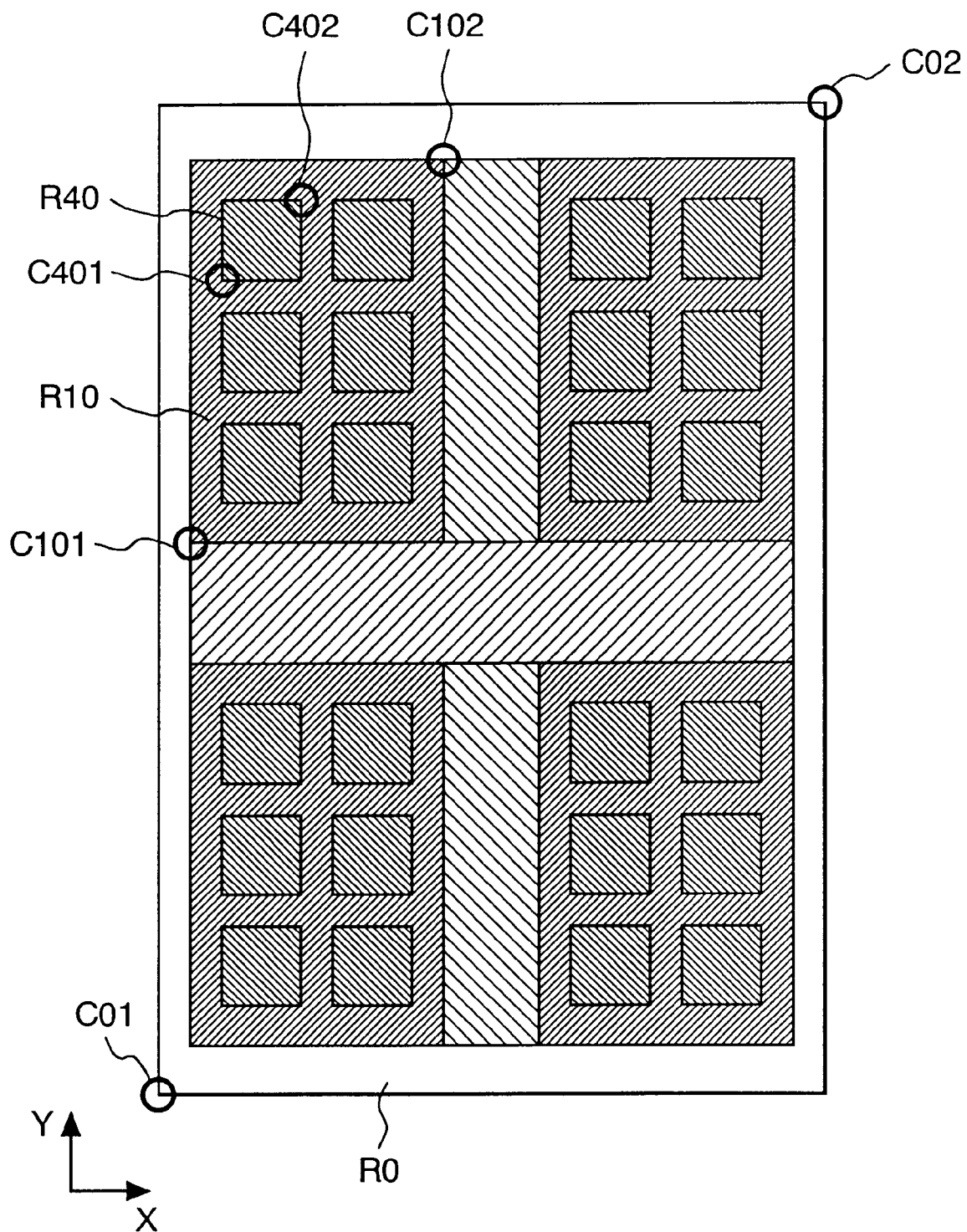
FIG. 2 is a chip layout to illustrate a structure of circuit semiconductor devices.

FIG. 2 is a chip layout to illustrate a structure of circuit semiconductor devices.

FIG. 3 is a table to illustrate X-Y coordinates and class values corresponding to each of areas.

Figures 4, 5:
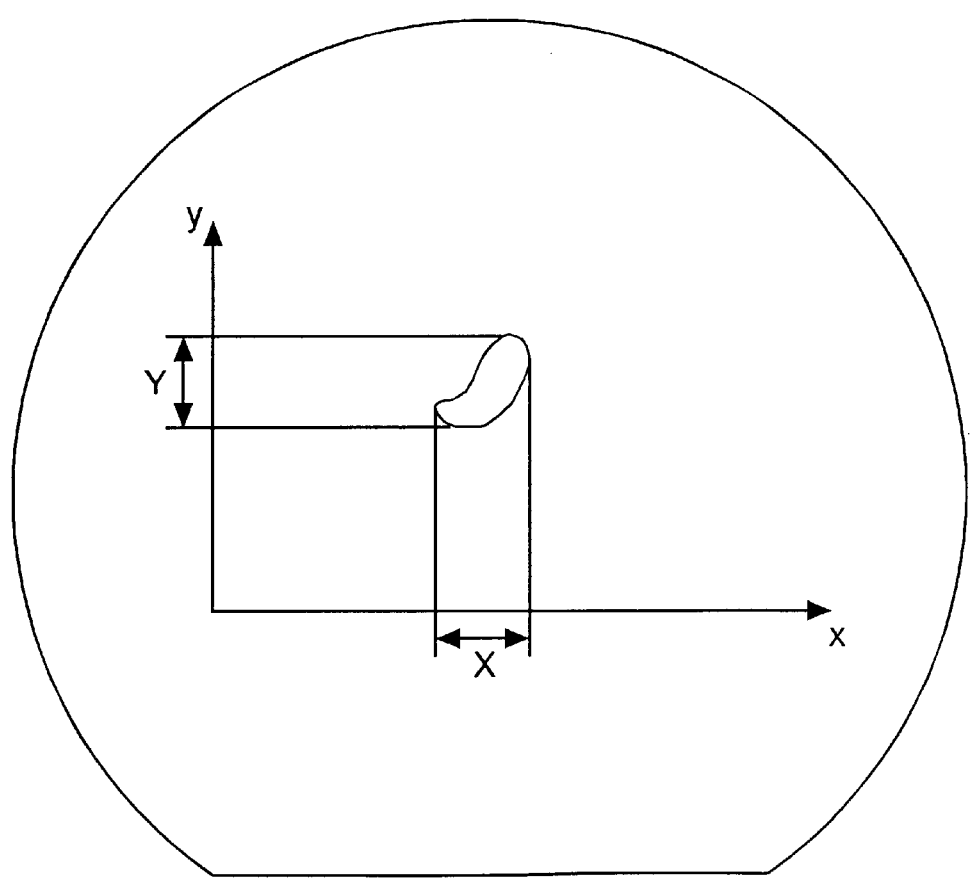
FIG. 4 is a table to illustrate a determination rule corresponding to each of class values.
FIG. 5 is a typical chart to illustrate the measurement principle of defects of the inspection instrument.

FIG. 4 is a table to illustrate a determination rule corresponding to each of class values.

FIG. 5 is a typical chart to illustrate the measurement principle of defects in the inspection instrument.

Figure 6:
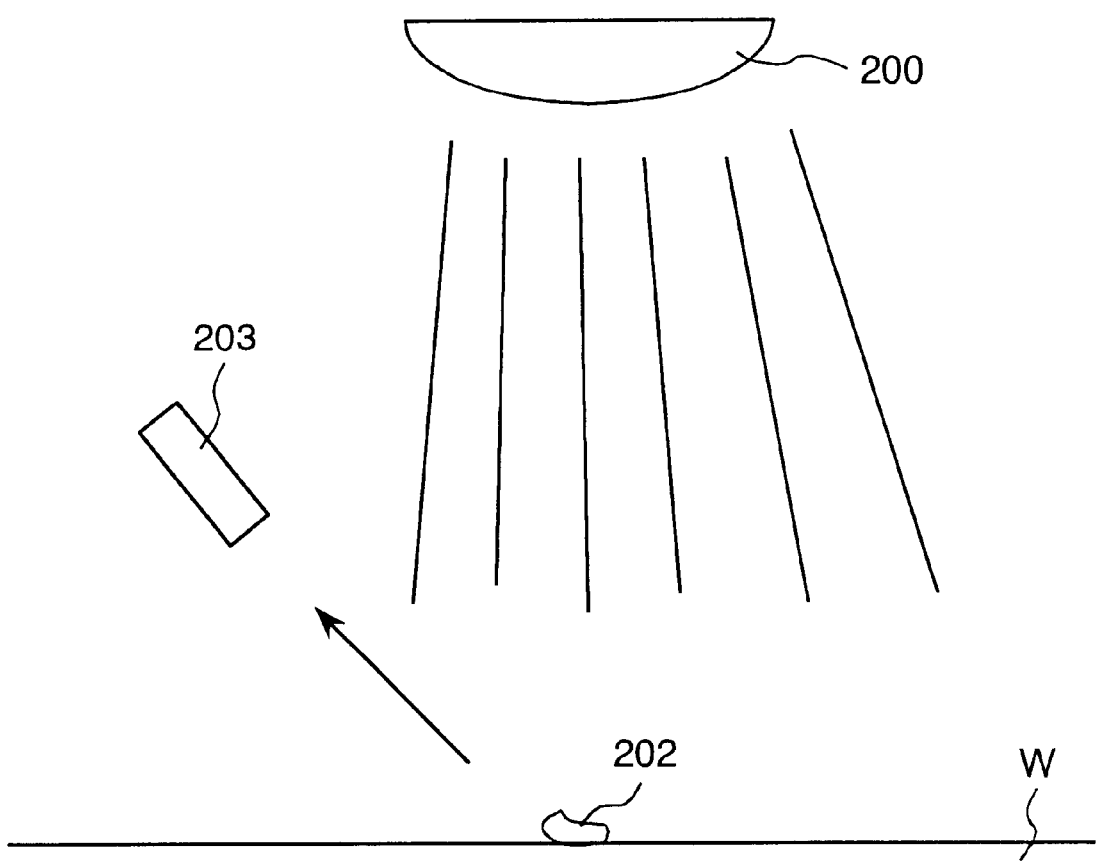
FIG. 6 is a typical chart to illustrate the principle of the dark field detection.

FIG. 6 is a typical chart to illustrate the principle of the dark field detection.

Figure 7:
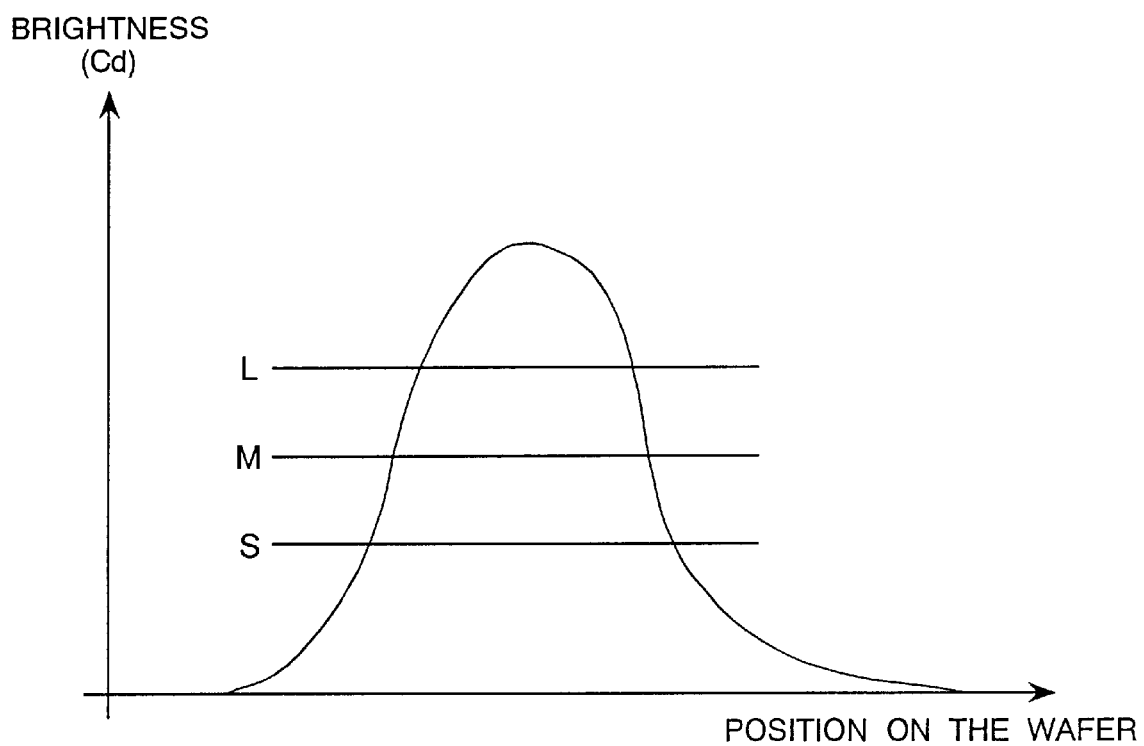
FIG. 7 is a chart to illustrate the distribution of a brightness being the output of a defect by the dark field detection.

FIG. 7 is a chart to illustrate the distribution of a brightness being the output of a defect by the dark field detection.

The chip areas indicate areas formed by dividing a chip into a plurality of areas according to, for example, the circuit pattern width in use, as shown in the chip layout in FIG. 2, and the areas each are illustrated in rectangles. Each of the areas is expressed by the coordinate at the lower left of the rectangle and the coordinate at the upper right thereof. For example, the area R0 can be expressed by the coordinates C01 and C02, the area R10 by the coordinates C101 and C102, and the area R40 by the coordinates C401 and C402.

The analysis system 1 of this embodiment divides a chip into each of the areas using the coordinates as shown in FIG. 3, and holds the class values corresponding to each of the areas. The class values are provided as the segments for inspecting for each of the areas. The analysis system contains a rule whereby the lethality of defects is determined for each of the class values, as described later.

The records in the table shown in FIG. 3 includes the area No., the lower left coordinates (X1, Y1) and upper right coordinates (X2, Y2) of each of the areas as the coordinate data of the chip areas, and the area class to indicate the classes of areas. The coordinate data of the chip areas are written in by a manual input, or by reading in a file from a CAD data. The origin of coordinates CO1 of the coordinate data chip areas is converted so as to coincide with the origin of the chip coordinates of the inspection instrument WI.

Next, the rule of determining the lethality of defects will be described with reference to FIG. 4 through FIG. 7.

The determination rule lethality of defects is the rule provided for each of the areas, whereby the size of a defect, namely, the lethality of a semiconductor defect is determined in the inspection.

This will be explained along with a concrete measurement method of the inspection instrument WI.

A defect on a semiconductor wafer is measured by way of the size or the area of the defect that is illustrated by the vertical and horizontal dimensions as shown in FIG. 5.

The defect becomes larger, as the X, Y becomes larger.

If the size of the defect is conceived to be expressed by the area A detected by the inspection instrument, the following expression 1 is introduced.

$$S_S = \sqrt{A} \qquad \text{(expression 1)}$$

Or, if the size of the defect is expressed by the length, the following expression 2 and expression 3 are given.

$$S_L = \sqrt{X \cdot Y} \qquad \text{(expression 2)}$$

$$S_L = \text{Max}(X, Y) \qquad \text{(expression 3)}$$

From another view, the size of the defect can be expressed by the brightness of the defect when detected. FIG. 6 illustrates the principle of the dark field detection. This detection method is to detect a defect 202 on a semiconductor wafer W in such a manner that a laser beam source 200 irradiates laser beams 201 on the semiconductor wafer W, and a detecting device 203 detects the brightness of laser beams reflecting from the defect. That is, as the defect is larger, the light area becomes wider; and the location and size of the defect can be measured from the shape of the graph shown in FIG. 7. In this example, the size of the defect is classified into L-size, M-size, and S-size, and when a measured brightness exceeds the lines (indicated by S, M, L), the defect is classified as a defect of the concerned size.

With these concepts, the determination rule is established such that when, to the area corresponding to the class value, the measured value there at exceeds the value given in the table in FIG. 4, the defect is considered as lethal.

FIG. 4 is a table that illustrates the correspondence between the data and the class values pertaining to this determination rule, concretely in terms of the length, area, and brightness.

Accordingly, in terms of the length, if the following expression 4 is met, the defect is determined as lethal.

$$S_L \geq R_L \qquad \text{(expression 4)}$$

In terms of the area, if the following expression 5 is met, the defect is determined as lethal.

$$S_S \geq R_S \qquad \text{(expression 5)}$$

In terms of the brightness, if the brightness exceeding the L, M, S size in the table is measured, the defect is determined as lethal, and it is characterized by the following expression 6.

$$S_B \geq R_B \qquad \text{(expression 6)}$$

Here, $S_B$ is the maximum value of the brightness of the graph illustrated in FIG. 7, and $R_B$ assumes either one of the brightness of L-size, M-size, and S-size.

These values $R_L$, $R_S$, $R_B$ can be conceived as the thresholds defect size that indicate the thresholds of the size of a defect relating to the area corresponding to the class value.

The data in this table can be determined from the design value of the representative pattern width or pattern spacing in the area to be measured. The threshold defect size $R_L$ may take the equal value to the design value of the pattern width or pattern spacing. For example, as shown in FIG. 41 when the pattern width of a semiconductor circuit in an area is 0.25 [μm], the threshold defect size $R_L$ can be set to the same value 0.25 [μm] at the class value 0.

Next, referring to FIG. 8, the method of determining the lethality of defects in the circuit pattern inspection relating to this embodiment will be described.

Figure 8:
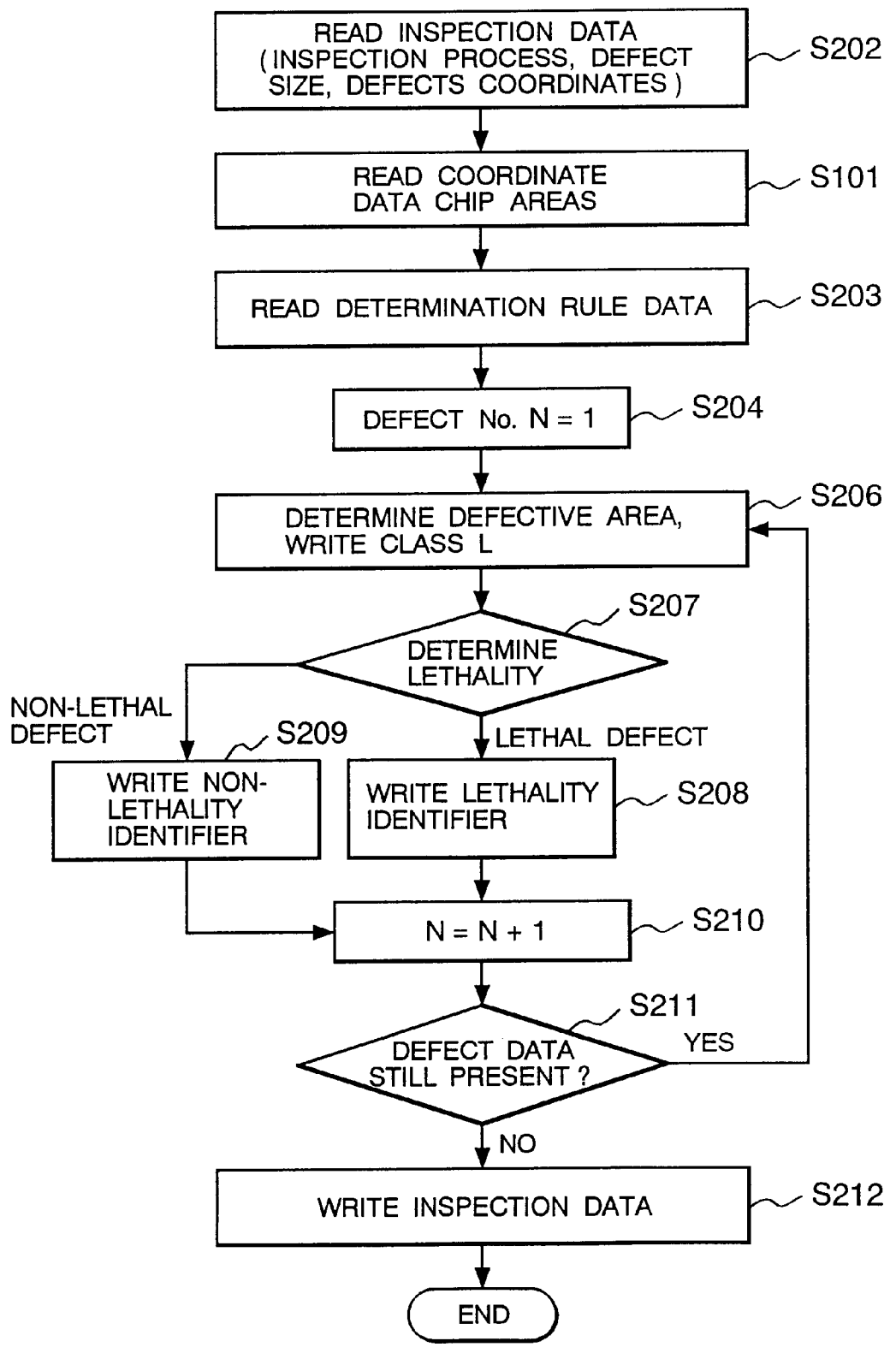
FIG. 8 is a flowchart to illustrate a method of determining the lethality of defects in the circuit pattern inspection relating to the first embodiment of the invention.

FIG. 8 is a flow chart to illustrate the method of determining the lethality of defects in the circuit pattern inspection relating to the first embodiment of the invention.

The determination method lethality defect will be explained along with the flow chart in FIG. 8.

First, the retrieval unit 5 retrieves the inspection data relating to the inspection process, coordinates of defects, sizes of defects, etc. stored in the inspection data storage unit 21 shown in FIG. 1, and the analysis system 1 accepts them in the memory 6 (S202). The defect No. is assumed to be assigned to each of the defects.

The analysis system 1 accepts the coordinate data chip areas from the storage unit for coordinate data chip areas 23 (S101).

The retrieval unit 5 retrieves the determination rule data corresponding to the inspection process accepted at step S202 from the storage unit for determination rule data 24, which are accepted in the memory 6 (S203).

The determination rule data are the data as already shown in FIG. 4.

Next, a defective area is determined from the defect coordinates (x, y) accepted at step S202, and the class value L corresponding to the defective area is written in the memory 6 (S206).

This is a preparation for determining the lethality of defects that switches the determination rule data referring to the class value corresponding to this area.

The determination of a defective area depends on whether the following expression 7 is satisfied for each area No., using the data in FIG. 3.

$$X1<x<X2, Y1<y<Y2 \qquad \text{(expression 7)}$$

The class value corresponding to a chip area is arranged to be overwritten in the order of the area No. With this arrangement, the class value corresponding to the larger area No. of the areas satisfying the expression 7 will automatically be written in the memory as the class value of the defect.

After completing the preparation, the lethality of defects is determined (S207).

That is, the class value L corresponding to the area of the defect of the defect No. N is read out, and the threshold defect size corresponding to the foregoing class value shown in FIG. 4 is compared with the measured value, thus determining the lethality. Concretely, the threshold defect size includes the length, area, and brightness, and the determination is made with the expressions 4, 5, and 6, as mentioned above.

If the defect is determined as lethal, the classification identifier F for the lethal defect is written in the memory 6 in correspondence with the defect of the defect No. N (S208). If the defect is determined as non-lethal, the classification identifier NF for the non-lethal defect is written in the memory 6 in correspondence with the defect of the defect No. N (S209).

Further, N is assigned by N+1 (N=N+1), and the counter is incremented (S210). If defect data are still present (S211), the process returns to the step S206 to continue the loop.

If defect data are not present (S211), the classification identifier F for the lethal defect and the classification identifier NF for the non-lethal defect which are written in the memory 6 at step S208 and S209, and the class value written in the memory 6 at step S206 are each written in the inspection data storage unit 21 in correspondence with each defect No. (S212).

Second Embodiment

The second embodiment relating to this invention will be described with reference to FIG. 9 through FIG. 11.

In the first embodiment, the coordinates brought into on a semiconductor wafer are employed in order to search defects on the semiconductor wafer. In the second embodiment, however, the coordinates on the semiconductor wafer are converted into the coordinates on the pixels, and thereafter the retrieval of defects and the assignment of class values are made.

First, referring to FIG. 9, the system construction of the circuit pattern inspection system relating to this embodiment will be described in detail as to the different parts from the first embodiment.

Figure 9:
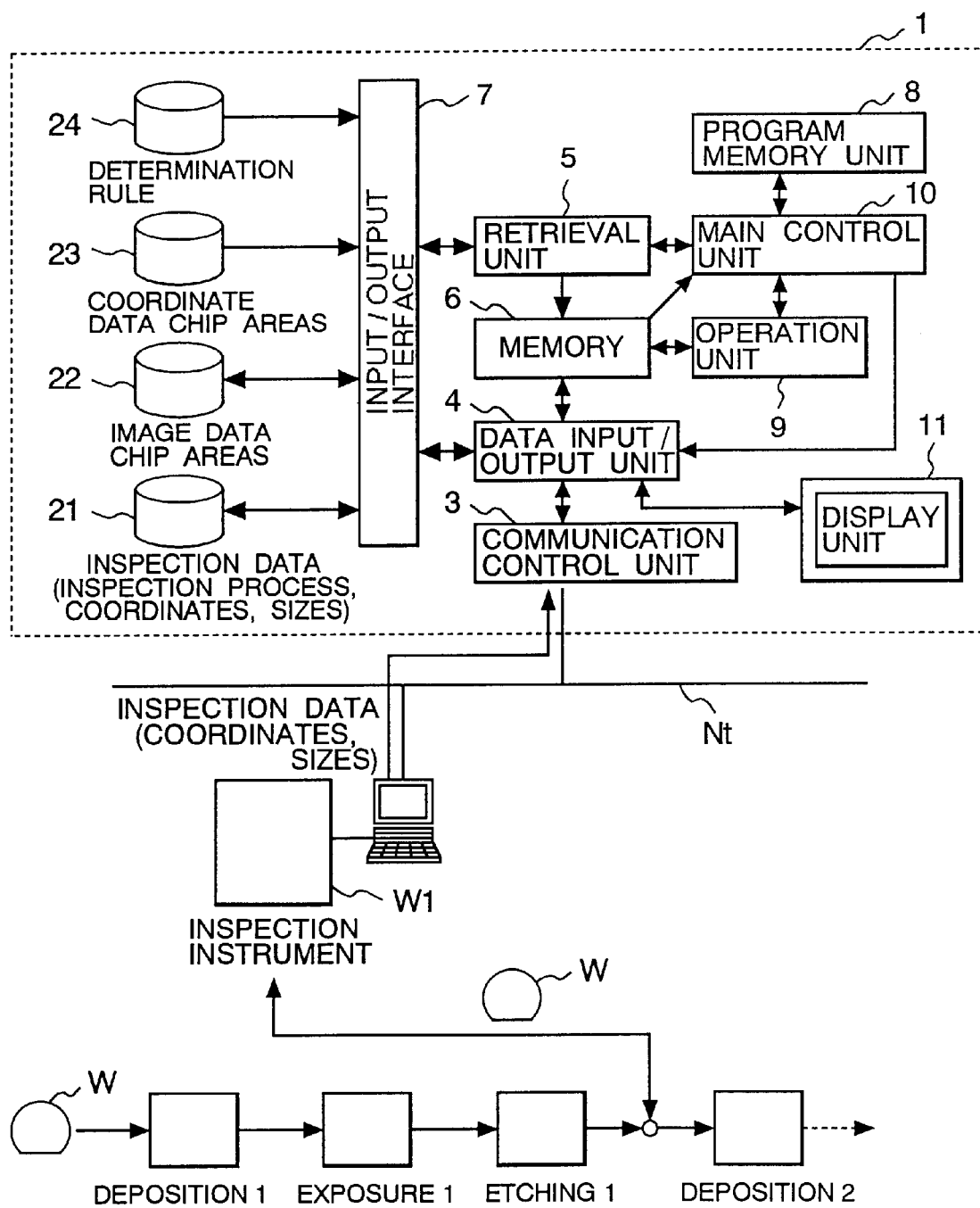
FIG. 9 is a block diagram of a circuit pattern inspection system relating to the second embodiment of the invention.

FIG. 9 illustrates a system construction of the circuit pattern inspection system relating to the second embodiment of the invention.

The circuit pattern inspection system of this embodiment is not substantially different from the first embodiment, however, the analysis system 1 further includes an image data storage unit chip areas 22, in addition to the construction of the first embodiment.

The image data storage unit chip areas 22 allows data read and data write in accordance with the instruction of the main control unit 10 through the input/output interface 7.

Next, referring to FIG. 10, a processing to assign a class value to each of the pixels of area image coordinates will be described.

Figure 10:
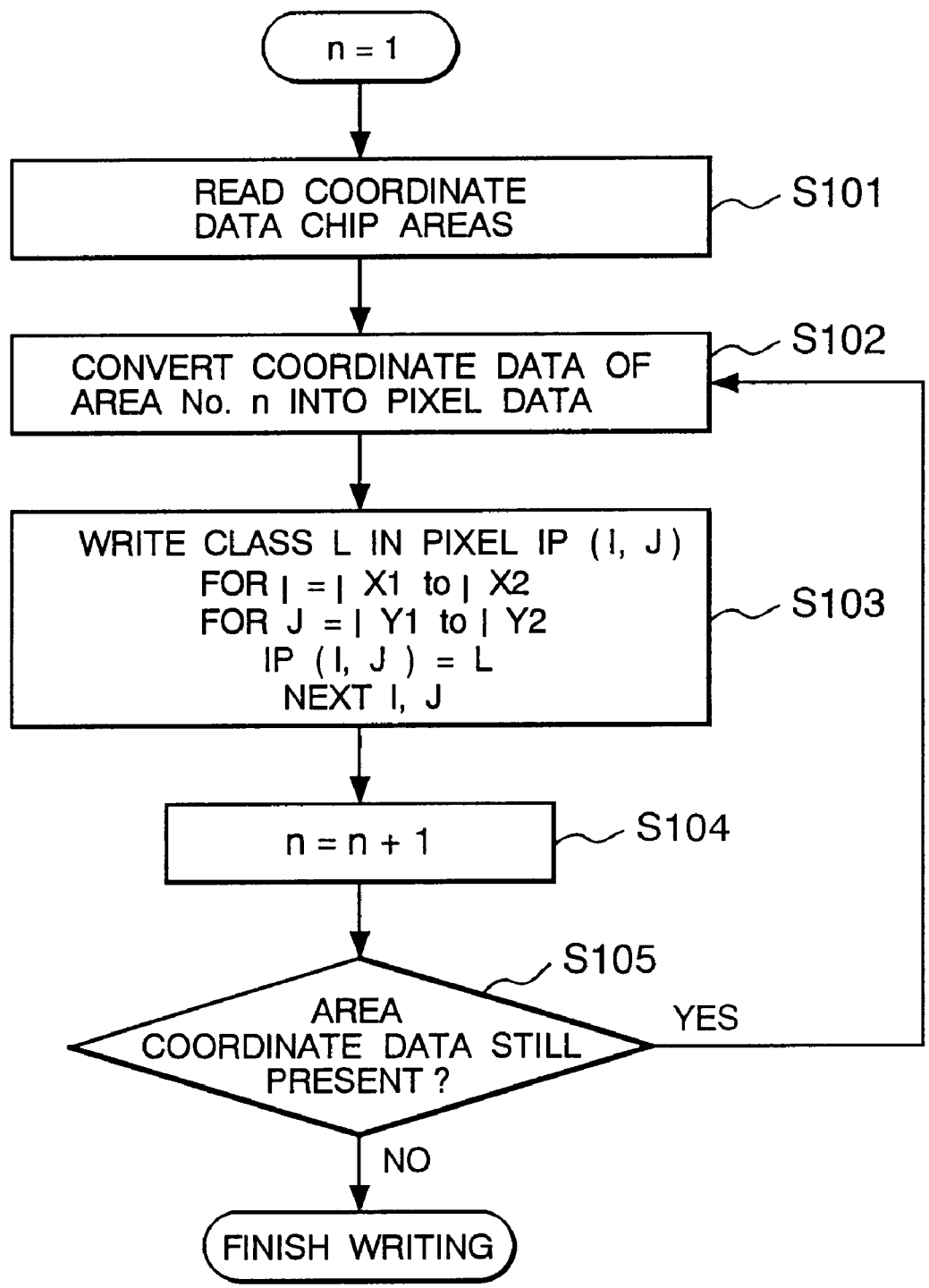
FIG. 10 is a flow chart to illustrate a processing to assign a class value to each of the pixels corresponding to the are image coordinates.

FIG. 10 is a flow chart to illustrate a processing to assign the class value to each of the pixels corresponding to the area image coordinates.

This processing can be called as the preparation processing in the method of determining the lethality of this embodiment.

First, the initial value is set in the counter (S100), and the retrieval unit 5 retrieves the coordinate data of chip areas stored in the storage unit for coordinate data chip areas 23, and the analysis system 1 accepts them in the memory 6 (S101).

Next, of the coordinate data of chip areas accepted at step S101, the area data of the area No. n is converted into the coordinates (pixel coordinates) of the area image data (S102).

That is, the lower left coordinates (X1, Y1) and the upper right coordinates (X2, Y2) of the areas corresponding to the coordinate data chip areas shown in FIG. 3 are converted into the pixel coordinates according to the following expression 8.

$$IX1 = Int\ (X1/P)$$
$$IX2 = Int\ (X2/P)$$
$$IY1 = Int\ (Y1/P)$$
$$IY2 = Int\ (Y2/P) \qquad \text{(expression 8)}$$

Here, P represents a preset pixel pitch, and Int represents the function to round down after the decimal point. The pixels in X, Y directions are assumed to take on the same scale pitch.

Next, the data of the class L are written in pixels IP (I, J) inside the area of a rectangle expressed by the converted pixel coordinates (IX1, IY1) and (IX2, IY2) (S103).

Further, the area No. n is assigned by n+1 (n=n+1), and the counter is incremented (S104), and whether the data of the area No. n are still present in the coordinate data chip areas is determined (S105). If the data are not present, the write-in is ended, the process goes out of the loop; and if the data are still present, the process returns to the step S102 to continue the loop.

The foregoing steps S102 to S104 is executed by the operation unit 9, and the determination at the step S105 is executed by the main control unit 10. If the main control unit 10 determines that the write-in is ended, the main control unit 10 stores the area image data IP (I, J) having been stored in the memory 6 into the image data storage unit chip areas 22 through the data input/output unit 4 and input/output interface 7.

Further, it may be arranged to save the memory capacity of the image data storage unit chip areas 22 in such a manner that the image data chip areas are compressed to be written in the image data storage unit chip areas 22 and uncompressed to be read out.

Next, the method of determining the lethality of defects in the circuit pattern inspection relating to this embodiment will be described with reference to FIG. 11.

Figure 11:
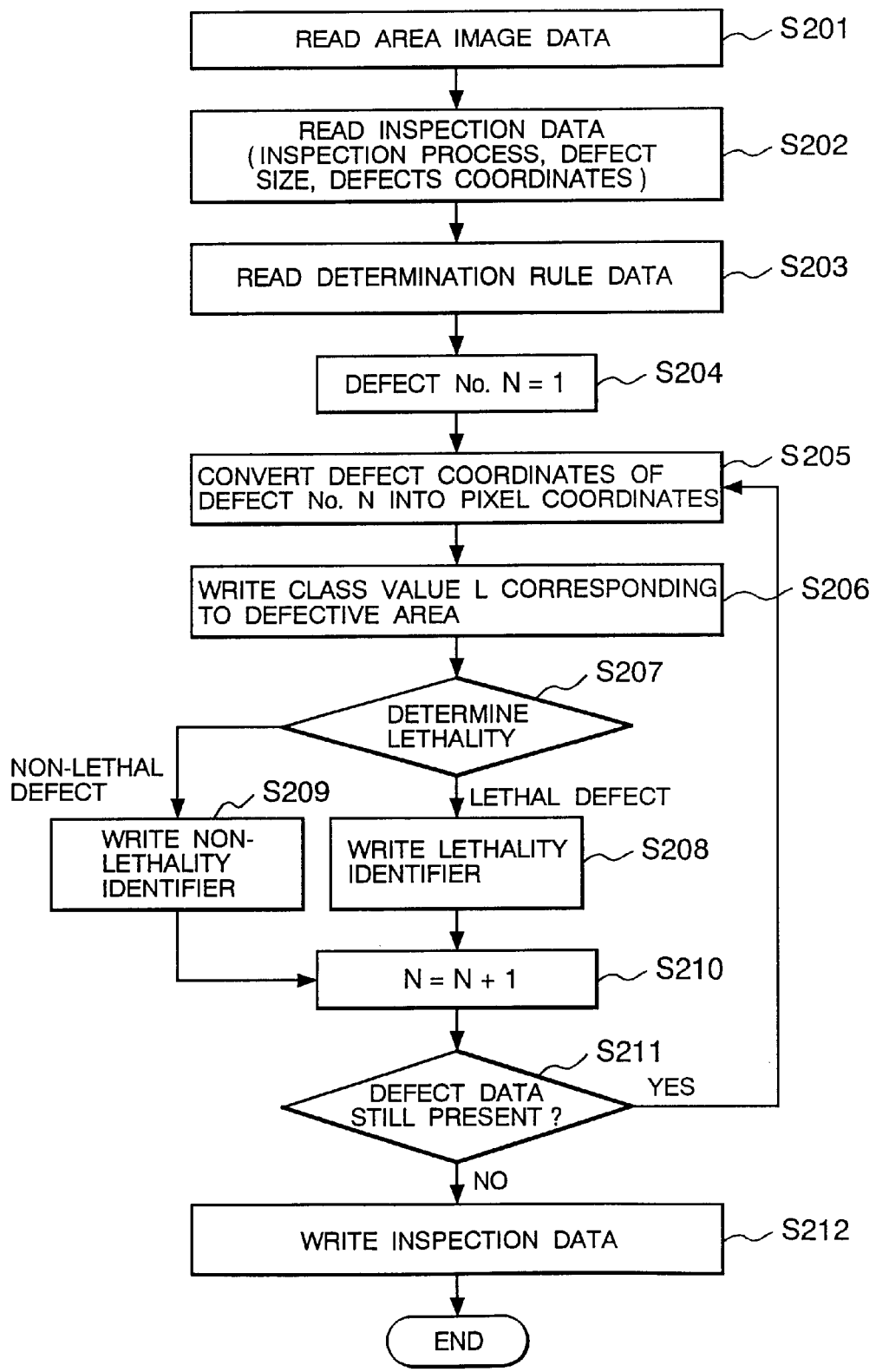
FIG. 11 is a flow chart to illustrate a method of determining the lethality of defects in the circuit pattern inspection relating to the second embodiment of the invention.

FIG. 11 is a flow chart to illustrate the method of determining the lethality of defects in the circuit pattern inspection relating to the second embodiment of the invention.

The different parts from the first embodiment will mainly be described, referring to the flow chart in FIG. 11.

First, the retrieval unit 5 retrieves the image data chip areas stored in the image data storage unit chip areas 22, and the analysis system 1 accepts them in the memory 6 (S201). The data here are the data in which the class values are assigned to the pixel coordinates, as mentioned above.

Next, the retrieval unit 5 retrieves the inspection data relating to the inspection process, coordinates of defects, sizes of defects, etc. stored in the inspection data storage unit 21 shown in FIG. 1, which are accepted in the memory 6 (S202).

Further, the retrieval unit 5 retrieves the determination rule data corresponding to the inspection process accepted at step S202 from the storage unit for determination rule data 24, and the analysis system 1 accepts them in the memory 6 (S203).

The determination rule data are the data as already shown in FIG. 4, in which the thresholds defect size $R_L$, $R_S$, $R_B$ corresponding to the class value L are written in.

Next, the counter of the defect No. N is initialized by N=1 (S204).

The defect coordinates (x, y) of the defect No. N are converted into the pixel coordinates (KX, KY) by the following expression 9 (S205).

$$KX = Int\ (x/P)$$
$$KY = Int\ (y/P) \qquad \text{(expression 9)}$$

Here, P represents a preset pixel pitch, which assumes the same value as in the expression 8.

Further, IP (KX, KY) corresponding to the value of the Epixel coordinates (KX, KY) of the area image data accepted at step S201, namely, the class value L corresponding to the concerned area is written in the memory 6 (S206).

Next, the lethality is determined from the defect sizes ($S_L$, $S_S$, $S_B$) of the defect No. N based on the determination condition (expression 4), (expression 5), (expression 6), and thresholds defect size ($R_L$, $R_S$, $R_B$) corresponding to the class values L (S207).

If the defect is determined as lethal, the classification identifier F for the lethal defect is written in the memory 6 in correspondence with the defect of the defect No. N (S208). If the defect is determined as non-lethal, the classification identifier NF for the non-lethal defect is written in the memory 6 in correspondence with the defect of the defect No. N (S209).

Next, N is assigned by N+1 (N=N+1), and the counter of the defect No. N is incremented (S210).

Whether the inspection data still include defects to be investigated is determined (S211); and if the data still remain, the process returns to the step S205 to continue the loop. If the defects to be investigated do not remain, the process will be finished. Here, the classification identifier F for the lethal defect and the classification identifier NF for the non-lethal defect which are written in the memory 6 at step S208 and S209, and the class value L written in the memory 6 at step S206 are each written in the inspection data storage unit 21 in correspondence with each defect No., as the final step (S212).

As in this embodiment, to assign the class values in advance to the image data so as to utilize them makes it possible to acquire the class value corresponding to the very defective area in a higher speed, which is advantageous.

Third Embodiment

Next, the third embodiment relating to the invention will be described with reference to FIG. 12 through FIG. 18.

Figure 12:
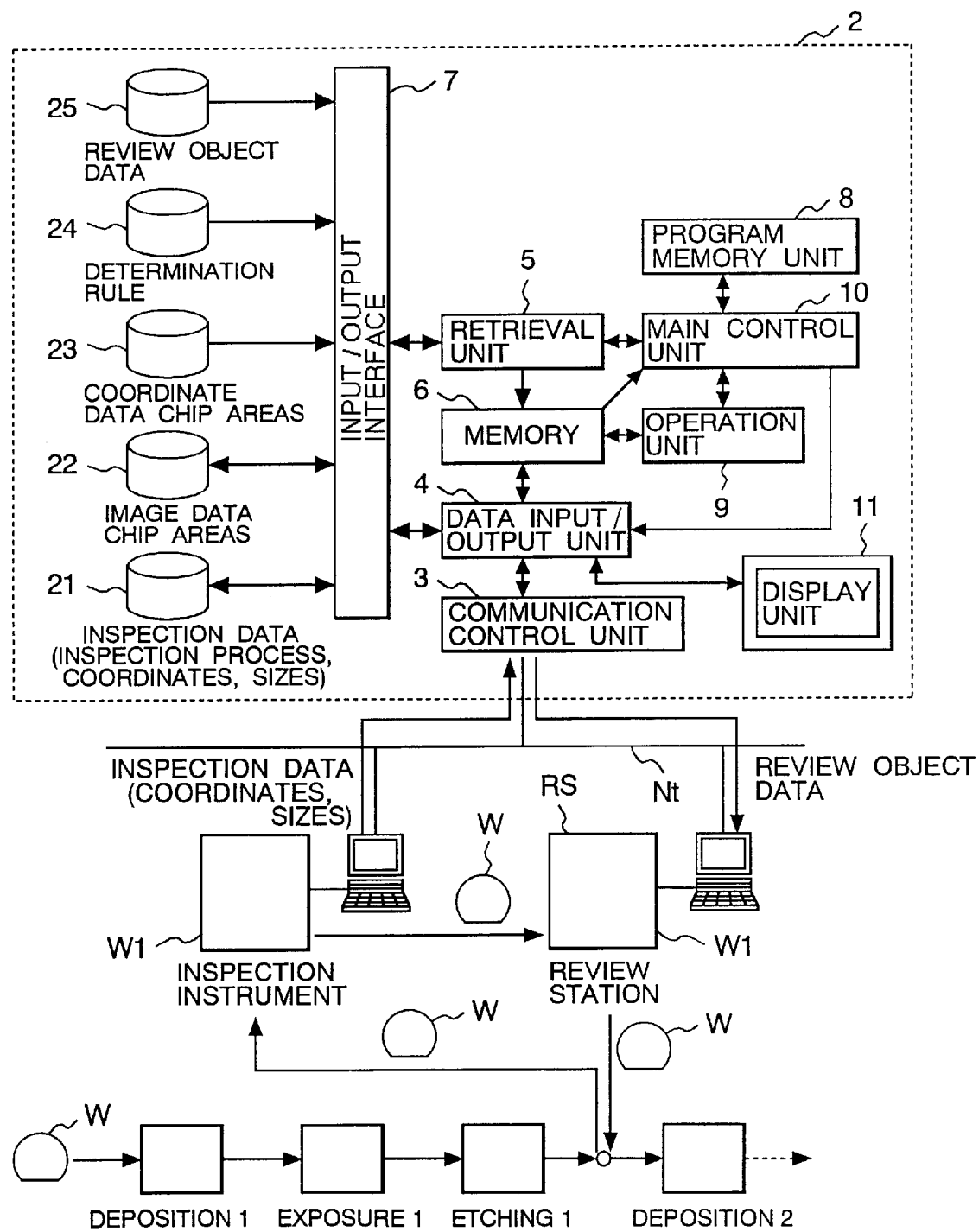
FIG. 12 is a block diagram of a circuit pattern inspection system having a function to select a defect treated as a review object of the invention.

First, referring to FIG. 12, the construction of the circuit pattern inspection system having a function to select a defect treated as a review object of this invention.

FIG. 12 illustrates a system construction of the circuit pattern inspection system having the selection function of a defect treated as a review object of the invention.

The circuit pattern inspection system having the selection function of a defect treated as a review object relating to this embodiment is provided with an analysis system 2, the inspection instrument WI, and a review station RS, which are connected to each other through the network Nt so as to exchange commands and data.

The review station is equipment that views the enlarged images of defects such as pattern shorts, pattern missing, particles, etc., from the optical microscope, scanning electron microscope, and the like to classify the defects.

The inspection instrument WI is equipment to inspect a semiconductor wafer W. The semiconductor wafer W is processed through a deposition system, exposure system, and etching system. Here, assuming that the semiconductor wafer W when the etching is completed is inspected, for example, the semiconductor wafer W is transferred to the review station RS, where the wafer W is reviewed and the defects are classified and analyzed. After the foregoing process is finished, the wafer W is returned to the processing process that resumes from the deposition system.

The coordinates of the defects and the data of the sizes outputted from the inspection instrument WI are stored in the inspection data storage unit 21 provided in the analysis system 2. The review station RS receives the coordinate data of defects to be reviewed from a review object data storage unit 25, and moves the stage to the position of a defect.

On the other hand, the analysis system 2 is similar to the construction of the second embodiment, and further contains the review object data storage unit 25.

As for the communication function, the analysis system 2 has the function to communicate with the inspection instrument WI, and in addition the function to communicate with the review station RS for exchanging commands and data, thereby exchanging review object data.

Further, the analysis system 2 of this embodiment has the function to select the review object, in addition to merely inspect the circuit patterns; and therefore, the analysis system 2 holds the programs to carry out these functions in the program memory unit 8.

Next, the method of selecting a defect treated as a review object in the circuit pattern inspection of this invention will be described with reference to FIG. 13.

Figure 13:
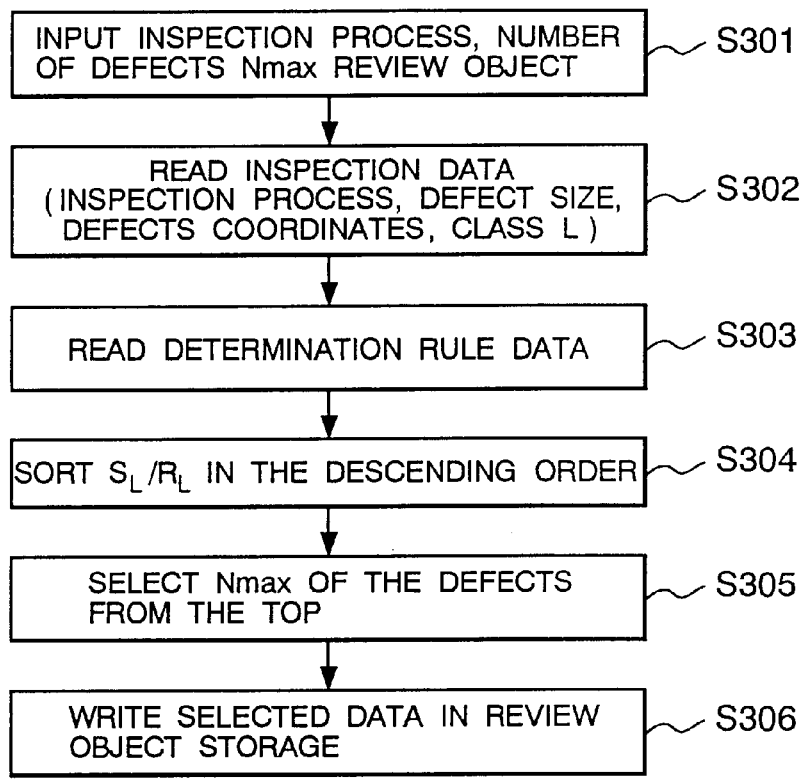
FIG. 13 is a flow chart to illustrate a processing procedure of a method of selecting a defect treated as a review object.

FIG. 13 is a flow chart to illustrate a processing procedure of the method of selecting a defect treated as a review object.

Here, the principle of selecting a review object will also be explained along with FIG. 13. Here, to simplify the explanation, the defect size takes on the length, the value defect size is given by $S_L$, and the threshold defect size is given by $R_L$; in the similar manner, the defect size may take on the area or the brightness in the dark field detection.

Here, it is assumed that before starting the process to select a defect treated as a review object, the process to determine the lethality of defects described in the first and second embodiment has be performed, and the classification identifiers of defects and the class values L have already been analyzed and written in the inspection data.

First, the inspection process to be reviewed and the defect selection number Nmax review object are inputted into the analysis system 1 by an input means such ad a keyboard (not illustrated). The analysis system 1 transfers the inputted data through the data input/output unit 4 to the memory 6, which stores them (S301). Here, the defect selection number Nmax review object is the upper limit number such that more than this number of reviews will not be executed.

Next, on the basis of the inspection process stored at step S301, the retrieval unit 5 retrieves the defect coordinates, defect sizes, and class values L of the concerned inspection process stored in the inspection data storage unit 21, and the analysis system 1 accepts them in the memory 6 (S302).

Next, the retrieval unit 5 retrieves the determination rule data from the storage unit for determination rule data 24, which are accepted in the memory 6 (S303).

Further, the ratio $S_L/R_L$ of the defect size $S_L$ against the threshold defect size $R_L$ corresponding to the class value L is calculated for each defect. Generally, as this ratio is greater, the defect can be considered as more critical, namely, as having more necessity of the review. Accordingly, the ratio $S_L/R_L$ is sorted in the descending order (S304).

Next, Nmax number of defects are selected from the top of the data sorted in the descending order at step S304 (S305), which are written in the review object data storage unit 25 (S306).

In this case, the upper limit number treated as the review object data is determined at the first stage; however, when the ratio $S_L/R_L$ is more than a certain value, the defects may be regarded as critical to be selected as the review objects. Further, the order of the class having the priority in the review selection may be inputted at step S301, and the defects may be sorted on the basis of the order of the class having the priority at step S304.

This principle makes it possible to select a defect of the chip area to which a review operator should give a higher priority of the review.

Further, the maximum review selection number Icmax per chip in a wafer is inputted at step S301, and if the review selection number per chip exceeds Icmax during the selection of defects at step S305, a process may be added, wherein the selection of defects of the number exceeding Icmax is not allowed as the review object.

Thus, setting the upper limit of the review number per chip makes it possible to appropriately select the defects of review object from the whole wafer, even when defects cluster in one and the same chip.

Up to now have been described the method, principle, and processing procedure of selecting defects to be reviewed in the circuit pattern inspection of this invention, however, further improvements of this invention will be described next.

First, the method of selecting an appropriate review object in view of defects emerging by each process will be described with reference to FIG. 14 and FIG. 15.

Figure 14:
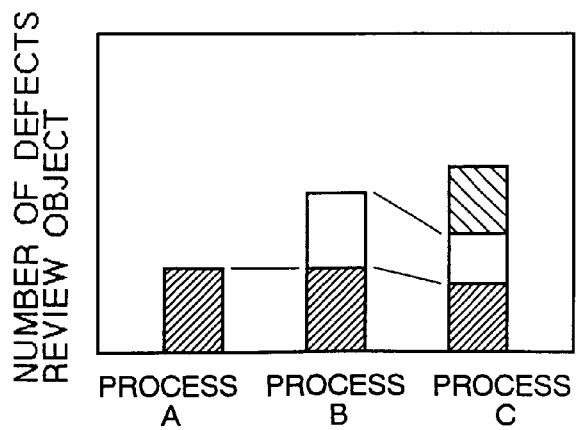
FIG. 14 is a bar graph to illustrate a transition of the number of defects treated as a review object by each process.

FIG. 14 is a bar graph to illustrate a transition of the number of defects review object by each process.

Figure 15:
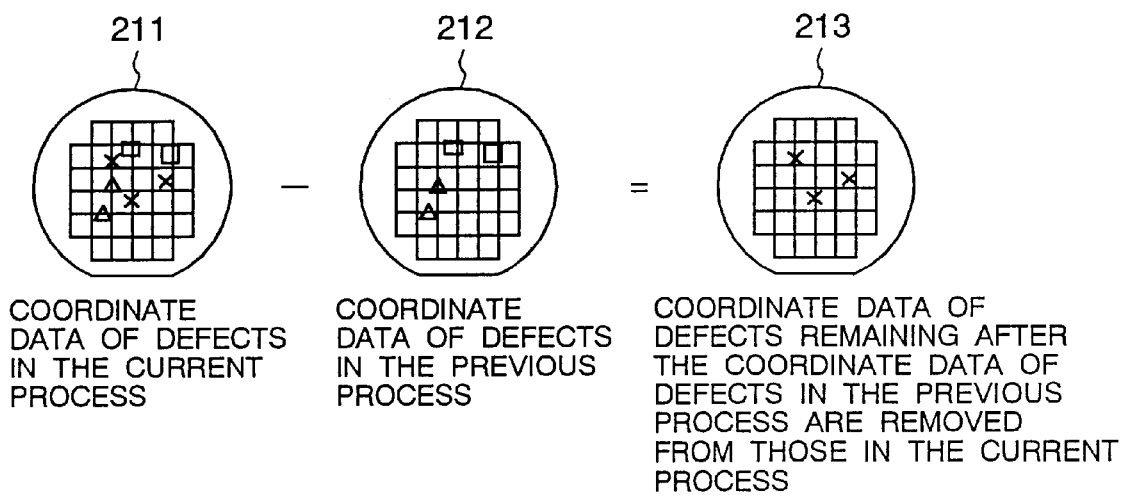
FIG. 15 is a typical chart to illustrate an example of a method to specify a process that causes a defect.

FIG. 15 is a typical chart to illustrate an example of a method to specify a process that causes a defect.

Generally, semiconductor devices are manufactured by repeating the processes of the deposition, exposure, and etching, while the inspection is carried out at each process.

The relation of cause and effect between the process and the number of emerging defects treated as review objects will now be examined. Suppose that a process A, process B, and process C are carried out in this order. Then, the number of the defects treated as review objects that are detected by each of the processes has a tendency as shown in FIG. 14. That is, as the proceeding advances to the subsequent processes, the defects generated in the previous processes are detected in accumulation.

Accordingly, in the review of defects performed after the subsequent process is finished, it is inefficient to consider the defects caused by the previous process. Therefore, in the selection of review objects, it is important to detect the defects generated by the concerned process only and treat the detected therein as the review objects.

Therefore, in this invention, each of the defects produced by each process is segmented and processed as follows.

FIG. 15 plots the coordinates of defects generated in a semiconductor wafer W typically by each process. The coordinate data 212 of defects detected in the previous process are expressed by □ and Δ, and the coordinate data 213 of defects generated only in the subsequent process (current process) are expressed by X. The coordinate data 211 of defects detected in the current process are the sum of the foregoing two coordinate data.

Therefore, the coordinate system of the coordinate data 211 of defects in the current process is aligned with that of the coordinate data 212 of defects in the previous process; and on the identical coordinate system, from all the coordinate data 211 of defects detected in the current process are subtracted the coordinate data 211 of defects in the current process that are coincident with or close within a preset allowance to the coordinate data 212 of defects detected in the previous process. As the result of the foregoing subtraction, the coordinate data 213 of defects that are newly generated in the current process are obtained, which are stored in the data storage unit review object 25 as defect data to be reviewed.

With this arrangement, only the defects generated in the current process can be selected as the review objects, and therefore, the defects already reviewed at the previous process will not be reviewed again, thus avoiding waste.

Next, the method of selecting a defect treated as a review object in which the relation between the process and the outbreak mode of defects is taken into consideration will be described with reference to FIG. 16 through FIG. 18.

Figure 16:
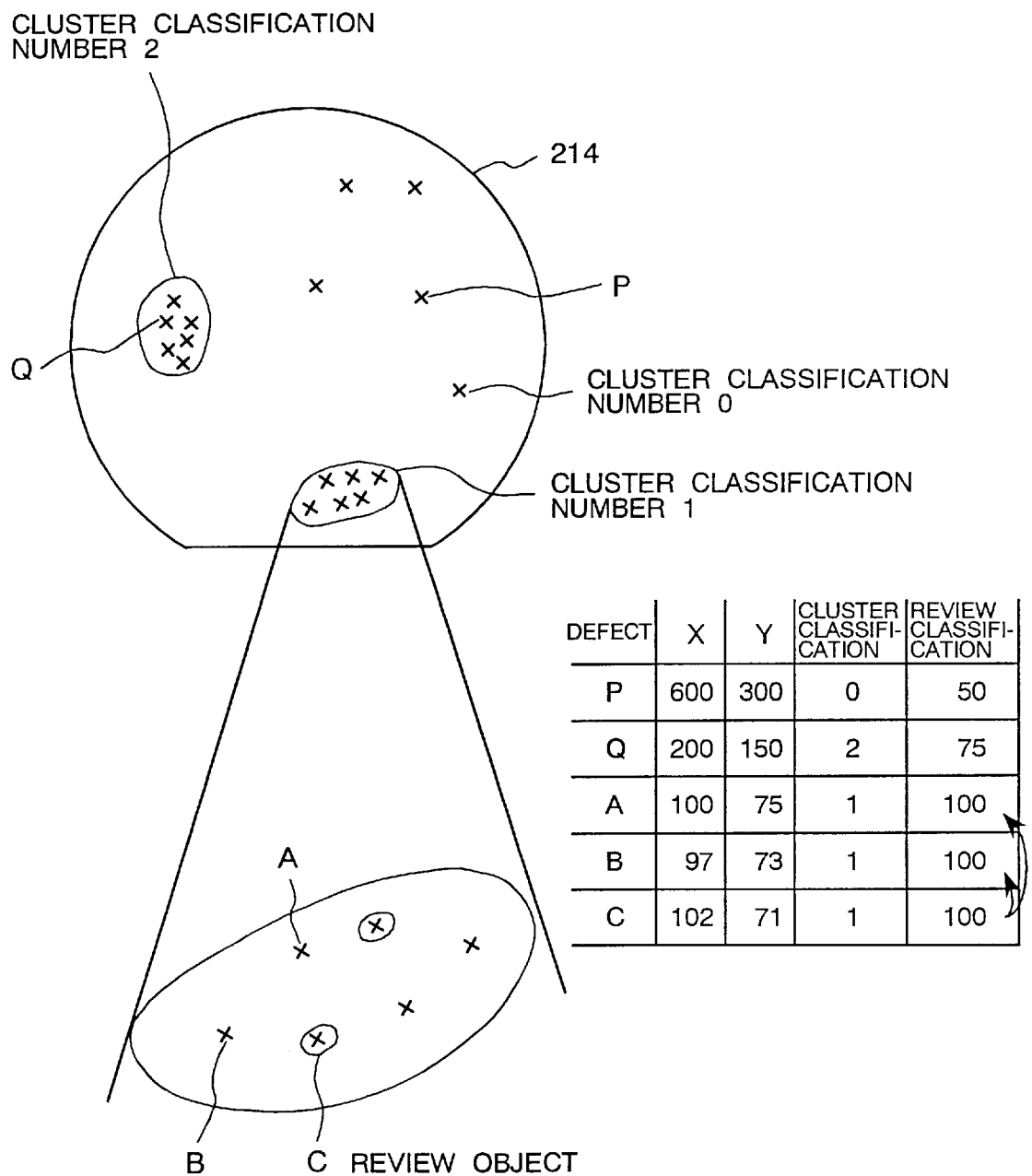
FIG. 16 is a typical chart to illustrate a state in which a review object is selected out of cluster defects.

FIG. 16 is a typical chart to illustrate a state in which a review object is selected out of cluster defects.

Figure 17:
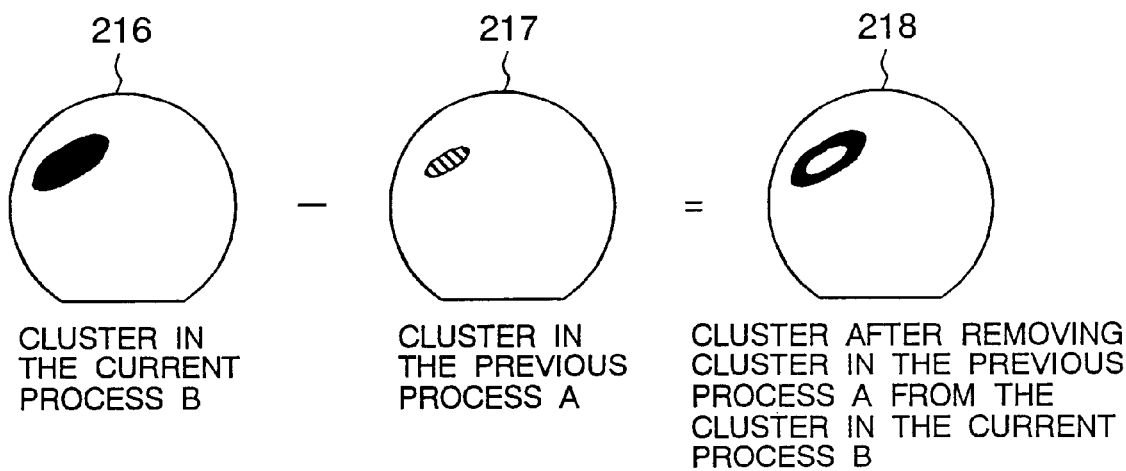
FIG. 17 is a chart to specify the process that causes cluster defects, which points out the problem in the conventional technique.

FIG. 17 is a chart to specify the process that causes cluster defects, which points out the problem in the conventional technique.

FIG. 18 is a typical chart to illustrate cluster defects generated in each process.

If a semiconductor wafer includes large defects, for example, scratches or the like, the inspection instrument WI detects the defects as groups of multiple defects, namely, cluster defects. The cluster defects are contrasted with the random defects that appear on a semiconductor wafer at random.

The conventional technique was inefficient to review the cluster defects, because the cluster defect data are registered as individual defect data in the inspection data storage unit 21, individual defects constituting a large defect have to be reviewed one by one, even if one and the same cause generates the large defect.

Accordingly in this invention, when cluster defects are detected, the review objects of the defects are classified in a reasonable manner as follows.

As shown in FIG. 16, the defects whose coordinate data are close are classified into cluster defects on a certain criterion. In FIG. 16, there are two cluster defects, which are classified into the cluster classification number 1 and the cluster classification number 2; and the other defects, namely, the random defects are given the cluster classification number 0.

On this condition, all the defects in one cluster are not made to be reviewed, and some of them are made to be reviewed. Here, it is assumed that the defect C is selected as a review object and the review classification number 100 is assigned thereto as the result of the review. The review classification number is a code to classify the results of the review (for example, pattern missing, pattern short-circuited, particles being present, etc.).

The defects having the same cluster classification number will not be reviewed, and the same review classification number as that of the defect C is assigned thereto. In this example, the review classification number 100 is also assigned to the defect A and defect B, the same as the defect C.

If a plurality of defects belonging to the same cluster are reviewed to acquire different review classification numbers, it is only needed to determine a rule in which a review classification number most found, for example, is picked up and that classification number is assigned to the defects belonging to the concerned cluster.

Thus, even if a wafer includes cluster defects being large defects such as scratches, it becomes possible to assign a review classification number for the whole cluster to all the defects belonging to the cluster only by the review of some defects constituting the cluster.

Further, in the foregoing cluster, a cluster of defects in a short distance is treated as a group. However, the grouping may be arranged such that the physical properties of defects such as the size, brightness, color, shape, and the like of defects detected by the inspection instrument are stored in the inspection data storage unit 21, and the defects are classified on the basis of these physical properties. Thus, in the other case than the cluster defects, the grouping of defects having the same physical properties and only the review of some defects in a group make it possible to assign a review classification number for the whole group to all the defects belonging to the group, in the same manner as the foregoing.

Next, a method of the review when the cluster defects generated in each process overlap will be described with reference to FIG. 17 and FIG. 18.

Here, it is assumed that the process A is the previous process and the process B is the current process.

In the defects on a semiconductor wafer, the previous process is likely to trigger a defect that will give an influence on the subsequent processes. Assuming that the defects in this case are in diffusion, the cluster mode will become such that the cluster 216 of the process B encloses the cluster 217 of the process A, as shown in FIG. 18(a).

Figure 18A:
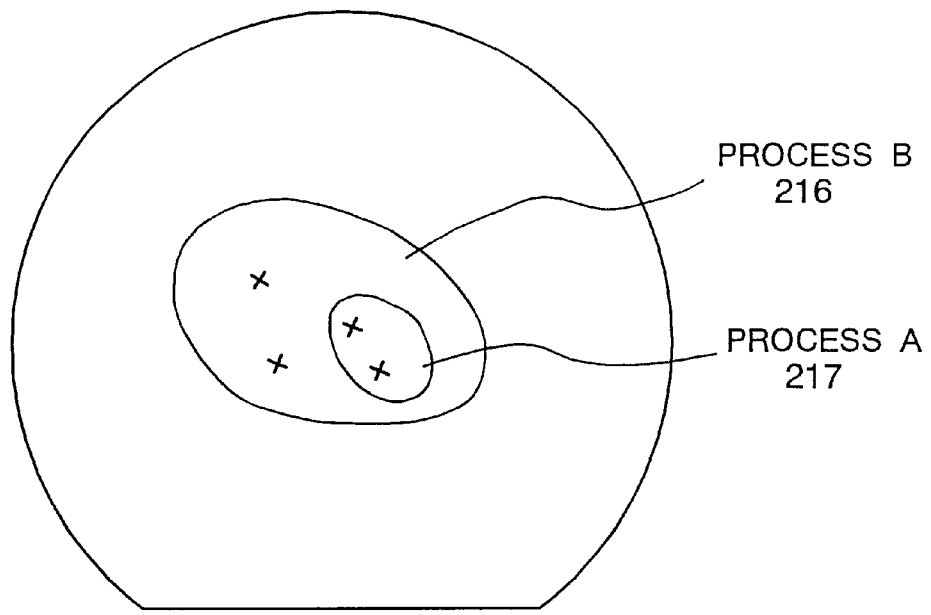
FIG. 18 is a typical chart to illustrate cluster defects generated in each process.
Figure 18B:
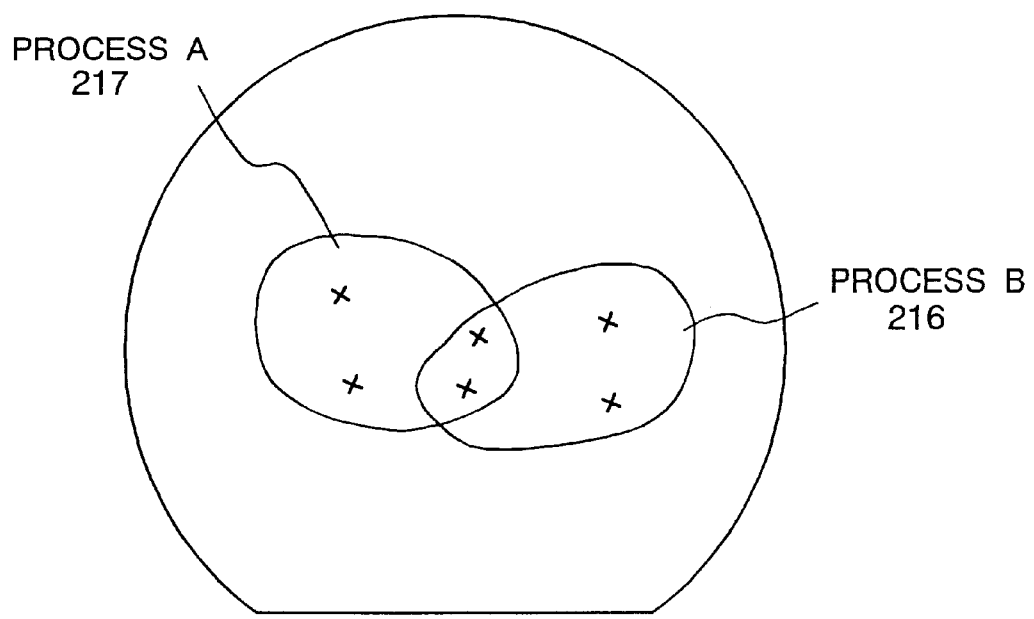
Figure 19A:
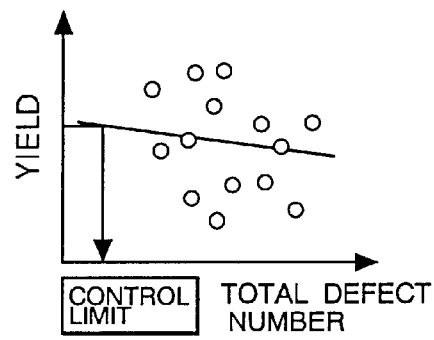
FIG. 19 illustrates a graph in which a relation between the total number of defects and the yield is plotted, and a graph in which the total number of defects generated in time series on each of inspection wafers is plotted.
Figure 19B:
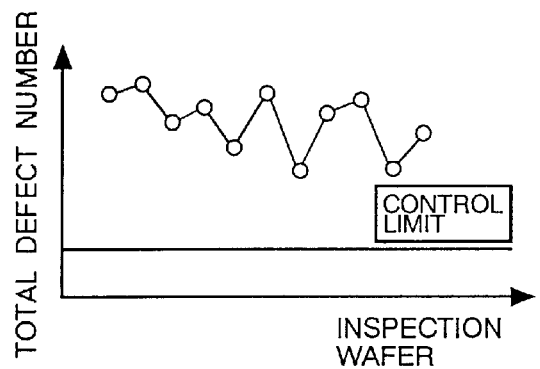

Although the cluster mode does not become the enclosure as shown in FIG. 18(a), there can be a case such that a part of the cluster is shared with each other as shown in FIG. 18(b), in case a defect of the process A induces a defect in the process B. Further, if the inspection instrument WI involves differences of the detection sensitivity between the processes; for example, if the detection sensitivity at the previous process A is lower than the detection sensitivity at the subsequent process B, there can be a case that the defect having already been generated in the previous process A is detected at the subsequent process B.

In such a case, to subtract the coordinate data formally as shown in FIG. 15 will hardly lead to a correct classification for the review. That is, in the cluster mode of FIG. 18(a), to subtract the cluster 217 of the previous process A from the cluster 216 of the current process B gives a doughnut-type cluster, as shown in FIG. 17; however, if this is regarded as the cluster of defects generated in the current process, it will be contrary to the fact.

Accordingly, when the same cluster defects are detected across the processes in this manner, the defects are assumed to be the ones that have been generated in the previous process. The review classification number obtained therein is made to be assigned to the defects belonging to both the clusters. This arrangement will eliminate the cluster defects detected across the processes from being reviewed individually in each process, and will further cancel the differences of sensitivities of the inspection instrument between the processes and enable the review in accordance with the cause to generate the cluster defects; and therefore, it becomes possible to maintain the quality of the review and enhance the efficiency of the review.

In an actual processing, based on the coordinates of individual defects belonging to the clusters of the process A and the process B, a cluster defective area is expressed as, for example, the maximum/minimum values of the coordinates of defects in the cluster (namely, the cluster is apprehended as a plane). If the cluster defective area of the process A includes an overlapping part with the cluster defective area of the process B, it is needed to add a processing that gives the same review classification number as that of the defects belonging to the cluster of the process A to all the defects belonging to the cluster of the process B.

In another processing, the whole wafer is divided into blocks each of which has about some hundred A m²to allocate addresses to the blocks, and the block that holds cluster defects is expressed as the address. If the cluster defective area of the process A includes an overlapping block with the cluster defective area of the process B, it may be arranged to add a processing which gives the same review classification number as that of the defects belonging to the cluster of the process A to all the defects belonging to the cluster of the process B.

Summary of the Embodiments

The invention will provide the method of determining the lethality of a defect that automatically determines the lethality of the defect without performing the review to enhance the efficiency of the inspection, when circuit patterns formed on a substrate such as a semiconductor wafer are inspected, and the inspection system to achieve the foregoing method.

Further, the invention will provide the method of automatically selecting a defect to be reviewed, whereby the review in the circuit pattern inspection can efficiently be performed and the quality of the inspection itself can be maintained, and the inspection system to achieve the same.

What is claimed is:

1. A method of inspecting defects of circuit patterns formed on a substrate, comprising the steps of:
   inputting inspection data of the defects existing on the circuit patterns inspected by an inspection apparatus;
   processing the inputted inspection data to determine the lethality of the defects; and
   displaying information relating to the lethality of defects on a display,
   wherein the lethality of the defects is determined based on a determination rule which is defined according to areas on the patterns.

2. A method of inspecting defects of circuit patterns formed on a substrate, according to claim 1, wherein the substrate comprises a plurality of areas having different characteristics, the determination rule is defined according to each of the areas on the patterns, and the inspection data are coordinate data of the circuit patterns and sizes of the defects.

3. A method of inspecting defects of circuit patterns formed on a substrate, according to claim 1, wherein each of the circuit patterns is segmented into several areas having different characteristics, and the data to determine the lethality of the defects are served as determination rules each provided for each of the areas of the circuit patterns.

4. A method of inspecting defects of circuit patterns formed on a substrate, comprising the steps of:
   (1) inputting area coordinate data of the circuit patterns;
   (2) inputting data regarding lethality of defects existing on the circuit patterns;
   (3) inputting coordinate data of defects detected on the circuit patterns and sizes of the defects;
   (4) identifying areas to which the defects belong, from the coordinate data of the defects;
   (5) comparing sizes of the defects with the data regarding the lethality of the defects by using the coordinate data of the defects to determine the lethality of the detected defects; and
   (6) displaying information of lethality of the detected defects determined in the step of comparing.

5. A method of inspecting defects of circuit patterns formed on a substrate, according to claim 4, wherein the sizes of the defects include length data, area data, and brightness data which are served as indexes when detecting the defects.

6. A method of inspecting defects of circuit patterns formed on a substrate, according to claim 4, wherein pattern widths or pattern spaces in the areas are used as the data to determine the lethality of the defects produced in the areas on the circuit patterns.

7. A method of inspecting defects of circuit patterns formed on a substrate, comprising the steps of:
   inputting inspection data of the defects existing on the circuit patterns inspected by an inspection apparatus;
   processing the inputted inspection data to select candidate defects to be reviewed;
   determining the defects to be reviewed among the selected candidate defects; and
   outputting information relating to the determined defects to be reviewed,
   wherein the selected candidate defects are lethality defects.

8. A method of inspecting defects of circuit patterns formed on a substrate, according to claim 7, wherein the inspection data are coordinate data of the circuit patterns and sizes of the defects.

9. A method of inspecting defects of circuit patterns formed on a substrate, according to claim 7, wherein each of the circuit patterns is segmented into several areas having different characteristics, and the data to determine the lethality of the defects are served as determination rules each provided for each of the areas of the circuit patterns.

10. A method of inspecting defects of circuit patterns formed on a substrate comprising the steps of:
   (1) accepting area coordinate data of the circuit patterns;
   (2) accepting data to determine the lethality of the defects;
   (3) accepting coordinate data of the defects detected on the circuit patterns and sizes of the defects;

(4) identifying areas to which the defects belong, from the coordinate data of the defects detected on the circuit patterns;

(5) determining lethality of the detected defects by using information of the coordinate data and size data of the defects; and (6) selecting the defects to be reviewed among the defects whose lethality are determined.

11. A method of inspecting defects of circuit patterns formed on a substrate, according to claim 10, wherein the defects selected as the review object are the defects corresponding to a specific number of the ratios obtained at the step (5), sorted in the descending order.

12. A method of inspecting defects of circuit patterns formed on a substrate, according to claim 10, wherein the defects selected as the review object are the defects corresponding to the ratios obtained at the step (5) and have respectively a specific value or more.

13. A method of inspecting defects of circuit patterns formed on a substrate, according to claim 10, wherein the sizes of the defects include length data, area data, and brightness data which are served as indexes when detecting the defects.

14. A method of inspecting defects of circuit patterns formed on a substrate, according to claim 10, wherein pattern widths or pattern spaces in the areas are used as the data to determine the lethality of the defects produced in the areas on the circuit patterns.

15. A method of inspecting defects of circuit patterns formed on a substrate, according to claim 10, wherein, in selecting the defects treated as the review object for each process, the method further comprises a step that compares coordinate data of the defects having been detected as the defects in a previous process to a process where the review is being executed at present with coordinate data of the defects having been detected as the defects in the concerned process where the review is being executed at present, and treats only the defects having non-coincident coordinate data in the result of the comparison as candidate defects of the review object in the concerned process where the review is being executed.

16. A method of inspecting defects of circuit patterns formed on a substrate, according to claim 10, wherein the method further comprises a step that classifies the defects produced on the circuit patterns into cluster defects having a clustered mode and random defects produced at random from the mode in which the defects are produced, and selects the review object with different treatments for the cluster defects and the random defects.

17. A method of inspecting defects of circuit patterns formed on a substrate, according to claim 16, wherein several defects of the cluster defects are selected as the review object, and the review result of the several defects is assumed as the review result of all the defects belonging to the cluster to thereby simplify the review for the cluster defects.

18. A method of inspecting defects of circuit patterns formed on a substrate, according to claim 16, wherein, in selecting the defects treated as the review object for each process, when the cluster defects detected in the previous process and the cluster defects detected in the subsequent process have an overlapping part, both of the cluster defects are treated as the cluster defects detected in the previous process.

19. An apparatus for inspecting defects of circuit patterns formed on a substrate, comprising:

a first memory to store inspection data of the defects existing on the circuit patterns detected by the inspection apparatus;

a second memory to store a data for determining lethality of the defects;

a processor to process the inspection data stored in the first memory; and means to determine the lethality of the defects corresponding to the inspection data by using the data stored in the second memory and the inspection data processed by the processor.

20. An apparatus for inspecting defects of circuit patterns formed on a substrate, according to claim 19, wherein the inspection data are coordinate data of the circuit patterns and sizes of the defects.

21. An apparatus for inspecting defects of circuit patterns formed on a substrate, according to claim 19, wherein each of the circuit patterns is segmented into several areas having different characteristics, and the data to determine the lethality of the defects are served as determination rules each provided for each of the areas of the circuit patterns.

22. An apparatus for inspecting defects of circuit patterns formed on a substrate, comprising:

a first means to store area coordinate data of the circuit patterns;

a second means to store data to determine lethality of defects existing on the circuit patterns;

a third means to store coordinate data of defects detected on the circuit patterns and sizes of the defects;

a fourth means to identify the areas to which the defects belong, from the coordinate data of the defects stored in the third means; and a fifth means to compare sizes of the defects detected with the data to determine the lethality of the defects produced in the areas on the circuit patterns where the defects belong to thereby determine the lethality of the defects.

23. An apparatus for inspecting defects of circuit patterns formed on a substrate, according to claim 22, wherein the sizes of the defects include length data, area data, and brightness data which are served as indexes when detecting the defects.

24. An apparatus for inspecting defects of circuit patterns formed on a substrate, according to claim 22, wherein pattern widths or pattern spaces in the areas are used as the data to determine the lethality of the defects produced in the areas on the circuit patterns.

25. An apparatus for inspecting defects of circuit patterns formed on a substrate, according to claim 22, wherein the inspection instrument and the analysis system are connected by a network, and the data and commands can be exchanged.

26. An apparatus for inspecting defects of circuit patterns formed on a substrate, comprising:

a first memory to store data of the defects existing on the circuit patterns, which are detected by an inspection apparatus;

a second memory to store data to determine a lethality of defects;

a first processor to determine the lethality of the defects stored in the first memory by using the data stored in the second memory; and a second processor to select defects to be reviewed among defects whose lethality is determined by the first processor.

27. An apparatus for inspecting defects of circuit patterns formed on a substrate, according to claim 26, wherein the inspection data are coordinate data of the circuit patterns and sizes of the defects.

28. An apparatus for inspecting defects of circuit patterns formed on a substrate, according to claim 26, wherein each of the circuit patterns is segmented into several areas having different characteristics, and the data to determine the lethality of the defects are served as determination rules each provided for each of the areas of the circuit patterns.

29. An apparatus for inspecting defects of circuit pasterns formed on a substrate, comprising:

a first memory to store area coordinate data of the circuit patterns;

a second memory to store data to determine the lethality of the defects existing on the circuit patterns;

a third memory to store coordinate data of defects detected on the circuit patterns and sizes of the defects;

means to identify the areas to which the defects belong, from the coordinate data of the defects stored in the third memory;

means to calculate the ratios of the sizes of the defects detected against the data to determine the lethality of the defects produced in the areas on the circuit patterns to which the defects belong; and means to select defects to be reviewed among the defects calculated by the means to calculate.

30. An apparatus for inspecting defects of circuit patterns formed on a substrate, according to claim 29, wherein the defects selected as the review object are the defects corresponding to a specific number of the ratios obtained by the means to calculate the ratios, sorted in the descending order.

31. An apparatus for inspecting defects of circuit patterns formed on a substrate, according to claim 29, wherein the defects selected as the review object are the defects corresponding to the ratios obtained by the means to calculate the ratios and have respectively a specific value or more.

32. An apparatus for inspecting defects of circuit patterns formed on a substrate, according to claim 29, wherein the sizes of the defects include length data, area data, and brightness data which are served as indexes when detecting the defects.

33. An apparatus for inspecting defects of circuit patterns formed on a substrate, according to claim 29, wherein pattern widths or pattern spaces in the areas are used as the data to determine the lethality of the defects produced in the areas on the circuit patterns.

34. An apparatus for inspecting defects of circuit patterns formed on a substrate, according to claim 29, wherein the system further comprises a review station to perform the review, the review station, the inspection instrument, and the analysis system are connected by a network, and thereby the data and commands can mutually be exchanged.

35. An apparatus for inspecting defects of circuit patterns formed on a substrate, according to claim 29, wherein, in selecting the defects treated as the review object for each process, the system further comprises means that compare coordinate data of the defects having been detected as the defects in a previous process to a process where the review is being executed at present with coordinate data of the defects having been defected as the defects in the concerned process where the review is being executed at present, and treats only the defects having non-coincident coordinate data in the result of the comparison as candidate defects of the review object in the concerned process where the review is being executed.

36. An apparatus for inspecting defects of circuit patterns formed on a substrate, according to claim 29, wherein the system further comprises means that classify the defects produced on the circuit patterns into cluster defects having a clustered mode and random defects produced at random from the mode in which the defects are produced, and selects the review object with different treatments for the cluster defects and the random defects.

37. An apparatus for inspecting defects of circuit patterns formed on a substrate, according to claim 36, wherein several defects of the cluster defects are selected as the review object, and the review result of the several defects is assumed as the review result of all the defects belonging to the cluster to thereby simplify the review for the cluster defects.

38. An apparatus for inspecting defects of circuit patterns formed on a substrate, according to claim 36, wherein, in selecting the defects treated as the review object for each process, when the cluster defects detected in the previous process and the cluster defects detected in the subsequent process have an overlapping part, both of the cluster defects are treated as the cluster defects detected in the previous process.

* * * * *